(12) United States Patent
Kolchin et al.

(10) Patent No.: US 9,726,617 B2
(45) Date of Patent: Aug. 8, 2017

(54) APPARATUS AND METHODS FOR FINDING A BEST APERTURE AND MODE TO ENHANCE DEFECT DETECTION

(71) Applicant: KLA-Tencor Corporation, Milpitas, CA (US)

(72) Inventors: Pavel Kolchin, Fremont, CA (US); Richard Wallingford, Forsyth, MO (US); Lisheng Gao, Saratoga, CA (US); Grace H. Chen, Los Gatos, CA (US); Markus B. Huber, Oakland, CA (US); Robert M. Danen, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 60 days.

(21) Appl. No.: 14/075,488

(22) Filed: Nov. 8, 2013

(65) Prior Publication Data
US 2014/0354983 A1    Dec. 4, 2014

Related U.S. Application Data

(60) Provisional application No. 61/830,858, filed on Jun. 4, 2013, provisional application No. 61/833,778, filed on Jun. 11, 2013, provisional application No. 61/867,517, filed on Aug. 19, 2013.

(51) Int. Cl.
*G01N 21/95*    (2006.01)
(52) U.S. Cl.
CPC ................... *G01N 21/9501* (2013.01)
(58) Field of Classification Search
CPC ................ G01N 21/00; G01N 21/9501

USPC ........................................ 356/237.5
See application file for complete search history.

(56) References Cited

U.S. PATENT DOCUMENTS

| | | | |
|---|---|---|---|
| 2,544,196 A * | 3/1951 | Varden | G01J 3/51 |
| | | | 355/38 |
| 7,001,055 B1 | 2/2006 | Lange | |
| 7,623,229 B1 * | 11/2009 | Vaez-Iravani et al. | 356/237.5 |
| 2006/0262297 A1 * | 11/2006 | Matsui et al. | 356/237.5 |
| 2009/0116727 A1 * | 5/2009 | Jin et al. | 382/149 |
| 2009/0232491 A1 | 9/2009 | Masuda et al. | |

(Continued)

FOREIGN PATENT DOCUMENTS

| KR | 20100069503 A | 6/2010 |
|---|---|---|
| KR | 20120039440 A | 4/2012 |

OTHER PUBLICATIONS

"International Application Serial No. PCT/US2014/040745, Search Report and Written Opinion mailed Oct. 1, 2014", 11 pgs.

(Continued)

*Primary Examiner* — Tarifur Chowdhury
*Assistant Examiner* — Omar Nixon
(74) *Attorney, Agent, or Firm* — Kwan & Olynick LLP

(57) ABSTRACT

Disclosed are methods and apparatus for optimizing a mode of an inspection tool. A first image or signal for each of a plurality of first apertures of the inspection tool is obtained, and each first image or signal pertains to a defect area. For each of a plurality of combinations of the first apertures and their first images or signals, a composite image or signal is obtained. Each composite image or signal is analyzed to determine an optimum one of the combinations of the first apertures based on a defect detection characteristic of each composite image.

23 Claims, 19 Drawing Sheets

(56) References Cited

U.S. PATENT DOCUMENTS

2010/0128137 A1 5/2010 Guidash
2011/0292390 A1* 12/2011 Shibata et al. ............... 356/369

OTHER PUBLICATIONS

Andersson, Thord et al., "A fast optimization method for level set segmentation", Proceedings of the 16th Scandinavian Conference on Image Analysis (SCIA). Oslo, Norway, 2009, 10 pgs.
Jehan-Besson, Stephanie et al., "DREAM2S: Deformable Regions Driven by an Eulerian Accurate Minimization Method for Image and Video Segmentation", International Journal of Computer Vision 53(1), 2003, pp. 45-70.
Sethian, J. A., "Level Set Methods and Fast Marching Methods Evolving Interfaces in Computational Geometry, Fluid Mechanics, Computer Vision, and Materials Science", Cambridge University Press, Retrieved from the Internet: https://math.berkeley.edu/%7Esethian/2006/Publications/Book/2006/OnLine/book_sethian.html, 1999, 2 pgs.

* cited by examiner

1. Use either experimental or simulation defect images obtained for different incoherent illumination directions that covers the entire illumination pupil space 2. For all *predefined aperture templates, spectrums, focus offsets, input and output polarization states* compute the composite camera images.

3. Then calculate Signal, Noise and Signal to Noise table for all defects and all modes (*predefined aperture templates, spectrums, focus offsets, input and output polarization states*)

4. Select the best mode that gives the highest Signal or SNR for an individual defect or a group of defect, for example, DOIs or select mode that gives the largest SNR separation between group of DOIs and Nuisance defects.

*Figure 11A*

1. Use either simulation data in the form of Jones scattering matrix or experimental defect imaging data obtained for different illumination direction that covers the entire illumination pupil space 2. For each defect, each spectrum, input and output polarization state and focus offset solve numerically the partial differential equation that describes the aperture edge evolution to find the optimized aperture.

3. Calculate composite image for the optimized aperture and Signal, Noise, SNR values 4. For each defect find the best mode (optimized aperture, spectrum, input and output polarization state and focus offset) based on SNR metric.

*Figure 12A*

APPARATUS AND METHODS FOR FINDING A BEST APERTURE AND MODE TO ENHANCE DEFECT DETECTION

CROSS-REFERENCE TO RELATED APPLICATION

This application claims priority to (i) U.S. Provisional Patent Application No. 61/830,858, filed 4 Jun. 2013, (ii), U.S. Provisional Patent Application No. 61/833,778, filed 11 Jun. 2013, and (iii) U.S. Provisional Patent Application No. 61/867,517, filed 19 Aug. 2013. These applications are incorporated herein by reference in their entirety for all purposes.

TECHNICAL FIELD OF THE INVENTION

The invention generally relates to the field of wafer and reticle inspection systems. More particularly the present invention relates to illumination pupil aperture and mode optimization for inspection tools.

BACKGROUND

As demand for ever-shrinking semiconductor devices continues to increase, so too will the demand for improved semiconductor wafer inspection systems. The fabrication of semiconductor devices, such as logic and memory devices, typically includes processing a semiconductor wafer using a large number of semiconductor fabrication processes to form various features and multiple levels of the semiconductor devices. Multiple semiconductor devices may be fabricated in an arrangement on a single semiconductor wafer and then separated into individual semiconductor devices.

Various inspection systems are used within the semiconductor industry to detect defects on a semiconductor reticle or wafer. In certain applications, the inspection system includes configurable apertures and modes.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for optimizing a mode of an inspection tool is disclosed. A first image or signal for each of a plurality of first apertures of the inspection tool is obtained, and each first image or signal pertains to a defect area. For each of a plurality of combinations of the first apertures and their first images or signals, a composite image or signal is obtained. Each composite image or signal is analyzed to determine an optimum one of the combinations of the first apertures based on a defect detection characteristic of each composite image.

In a specific implementation, the optimum combination of the first apertures is used to inspect a sample. In one aspect, each first image or signal is obtained from experimental data from a sample using each of the first apertures in the inspection. In another aspect, each first image or signal is obtained from a simulation model for the inspection tool obtaining the first image or signal using each first aperture.

In one embodiment, the first apertures are positioned at a plurality of pupil positions across a pupil of the inspection tool. In another aspect, the first apertures are positioned at a plurality of pupil positions across a Fourier plane of the inspection tool. In another aspect, the first apertures are individual apertures that together cover a substantial portion of the pupil or Fourier plane of the inspection tool. In a specific example, composite images are obtained for all combinations of the first apertures. In another embodiment the defect detection characteristic is a defect of interest (DOI) signal to noise signal ratio or a difference between a DOI signal and a noise signal, and the optimum combination of the first apertures has a composite image having a maximum DOI signal to noise signal or a maximum difference between a DOI signal and a noise signal. In a further aspect, the defect detection characteristic is determined for each of plurality of points within a region of interest (ROI) of each composite image.

In another aspect, the first images are further obtained for a plurality of modes having different combinations of wavelength range settings, focus offset settings, and input and output polarization states, and the composite images are further obtained for each of the modes. In a further aspect, the first images are obtained for a plurality of defect classes, and the composite images are further obtained for each of the defect classes. In another aspect, a plurality of optimum combinations of the first apertures are determined for two or more optimum ones of the modes that will together result in a separation of defect classes. For instance, the separation of defect classes comprises a separation between DOI's and nuisance defects.

In another method embodiment, an aperture of the inspection tool is opened one at a time at each of a plurality of aperture positions that are spread across an illumination pupil area or a Fourier plane area. While each aperture is opened at each aperture position, an incident beam of the inspection tool is directed towards one or more defect areas on a sample and an output beam emanating from each one or more defect areas in response to the incident beam is detected as such aperture either selectively transmits/reflects a portion of the incident beam or collects a portion of the output beam. Based on the output beam or the output beam portion, a defect detection characteristic for each aperture position and combination of aperture positions is determined. An optimum aperture configuration is determined based on the determined defect detection characteristic for each aperture position.

In a specific embodiment, opening an aperture at each of the plurality of aperture positions causes different incident angles of the incident beam on the sample. In a further aspect, opening a plurality of apertures at the plurality of aperture positions causes different portions of the output beam to be collected. In a further aspect, determining the defect detection characteristic for each aperture position and combination of apertures positions comprises: (i) generating an image of the defect area for each aperture position based on the detected output beam or output beam portion, (ii) summing the images for each combination of aperture positions to obtain a plurality of composite images, (iii) for each aperture position, determining a signal to noise value based on such aperture's image, (iv) for each aperture combination determining a defect of interest (DOI) signal to noise signal ratio or a difference between a DOI signal and a noise signal based on such aperture combination's composite image, and (v) defining an aperture combination that has a maximum defect of interest (DOI) signal to noise signal ratio or a maximum difference between a DOI signal and noise signal as the optimum aperture configuration.

In another aspect, the optimum aperture configuration is not yet available on the inspection tool. In yet another embodiment, the optimum aperture configuration is available on the inspection tool, and the method further includes using the optimum aperture configuration to inspect the sample for defects.

In an alternative method embodiment, opening an aperture of the inspection tool is simulated one at a time at each of a plurality of aperture positions that are spread across an illumination pupil area or a Fourier plane area. An image or signal of one or more defect areas for each aperture position of the inspection tool is simulated. Based on the simulated images and signals, a defect detection characteristic for each aperture position and combination of aperture positions is determined. An optimum aperture configuration is determined based on the determined defect detection characteristic for each aperture position.

In one aspect, opening an aperture at each of the plurality of aperture positions is associated with different incident angles of a simulated incident beam directed towards the one or more defect areas. In another aspect, opening a plurality of apertures at the plurality of aperture positions is associated with different portions of a simulated output beam emanating from the one or more defect areas. In a specific implementation, determining the defect detection characteristic for each aperture position and combination of apertures positions comprises (i) summing the images for each combination of aperture positions to obtain a plurality of composite images, (ii) for each aperture position, determining a signal to noise value based on such aperture's image, (iii) for each aperture combination determining a defect of interest (DOI) signal to noise signal ratio or a difference between a DOI signal and noise signal based on such aperture combination's composite image, and (iv) defining aperture combination that has that has a maximum defect of interest (DOI) signal to noise signal ratio or a maximum difference between a DOI signal and noise signal as the optimum aperture configuration. In one embodiment, the optimum aperture configuration is not yet available on the inspection tool. In another example, the optimum aperture configuration is available on the inspection tool, and the method further includes using the optimum aperture configuration to inspect the sample for defects.

In certain embodiments, the invention pertains to an inspection system for inspecting a photolithographic reticle or wafer for defects. The system includes a light source for generating an incident beam, a configurable illumination pupil aperture for receiving the incident beam, and an illumination optics module for directing the incident beam through the illumination aperture and onto a sample. The system also includes a collection optics module for directing an output beam that is emitted from the sample in response to the incident beam, a sensor for detecting the output beam and generating an image or signal for the output beam, and a controller configured to perform at least some of the above described operations. In other embodiments, the invention pertains to computer readable media having instructions stored thereon for performing at least some of the above described operations.

These and other aspects of the invention are described further below with reference to the figures.

BRIEF DESCRIPTION OF THE DRAWINGS

FIGS. 11A-11C illustrate processes for determining a best mode in accordance with one embodiment of the present invention.

FIGS. 12A-B illustrate a process for simulating an aperture configuration and evolving the simulated aperture edges in accordance with a specific implementation of the present invention.

DETAILED DESCRIPTION OF EXAMPLE EMBODIMENTS

Figure 1:
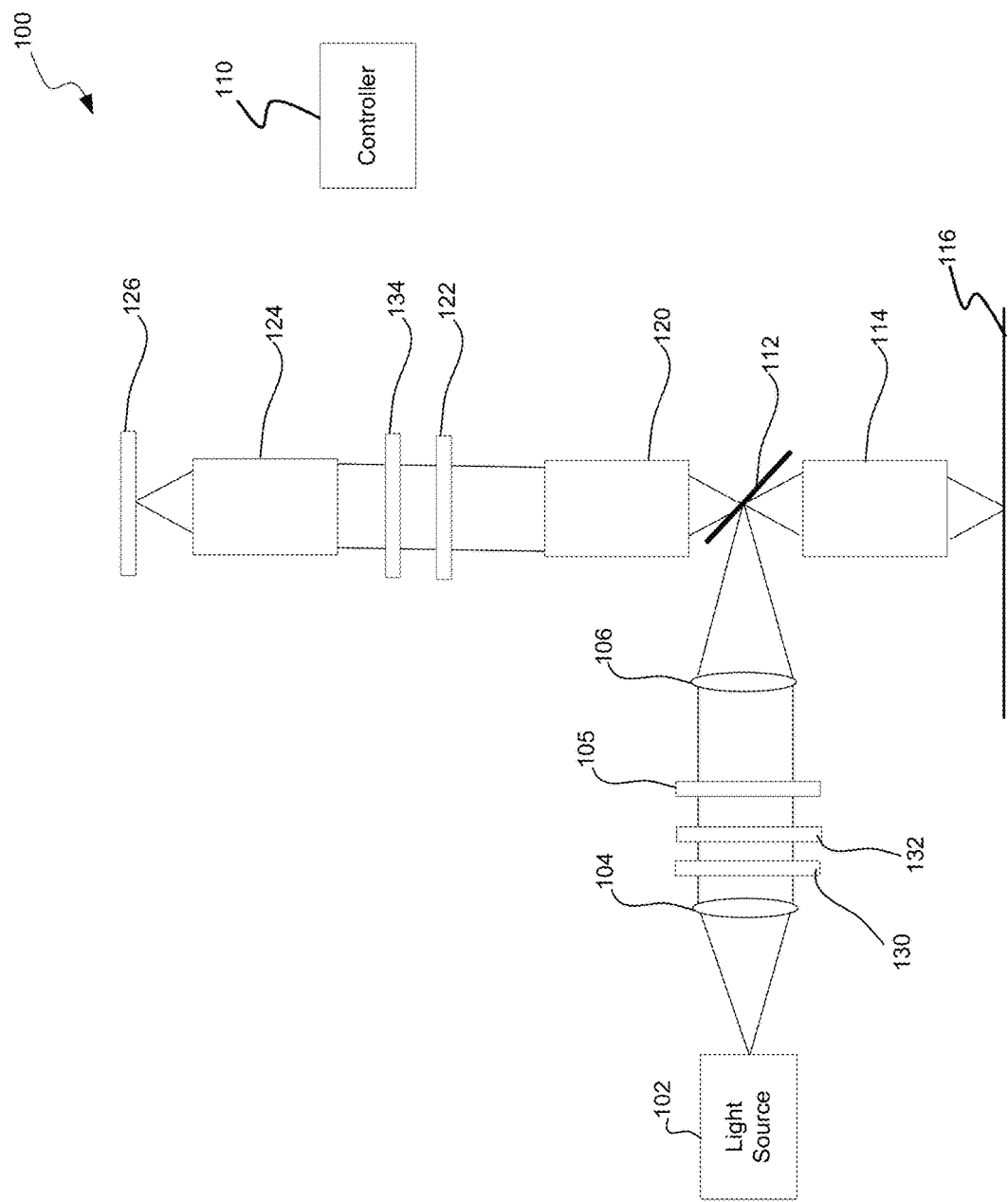
FIG. 1 is a diagrammatic representation of an example inspection apparatus.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Described herein are embodiments of an inspection apparatus and methods for quickly and comprehensively determining an optimum configuration of illumination and/or collection apertures to select or block optical illumination and/or collection beams in the pupil plane or Fourier plane on an inspection tool so as to enhance and optimize defect detection. For example, the shape of the apertures that results in the highest defect sensitivity is used for defect inspection. Additionally, certain embodiments of the present invention provide apparatus techniques for finding a best mode or combination of spectral band, focus offset, input and output polarizations, as well as best aperture configuration, so as to optimize and enhance defect detection. For instance, an optimum mode is found so as to maximize a ratio of defect of interest (DOI) signal to noise. Additionally, an optimum mode may be found so as to maximize the defects of interest (DOIs) that are detected while simultaneously minimizing the nuisance events that are detected.

Prior to describing specific embodiments for optimizing illumination pupil aperture configurations and inspection mode, general inspection systems will first be described. An inspection tool may include at least one light source for generating an incident light beam, configurable illumination pupil apertures for receiving the incident beam, illumination optics for directing the incident beam through the illumination aperture and onto a sample, configurable collection apertures, collection optics for directing an output beam that is emitted from the sample in response to the incident beam, a sensor for detecting the output beam and generating an image or signal for the output beam, and a controller for controlling the components of the inspection tool and facilitating the selection of one or more optimum illumination pupil aperture configurations or modes as described further herein.

In the following exemplary inspection systems, the incident beam may be in any suitable form of light. Different wavelengths can be selected to optimize for detecting defects with different characteristics, and a combination of several wavelengths can be advantageous for further reducing light coherence and averaging out the effect of wafer film thickness variations.

Additionally, any suitable lens arrangement may be used to direct the incident beam towards the sample and direct the output beam emanating from the sample towards a detector. The illumination and collection optical elements of the system may be reflective or transmissive. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

The inspection apparatus of the present invention are especially suitable for inspecting semiconductor devices or wafers, as well as reticles or masks. Other types of samples which may be inspected or imaged using the inspection apparatus of the present invention include any surface, such as a flat panel display.

FIG. 1 is a diagrammatic representation of an inspection system 100 in accordance with one embodiment of the present invention. As shown, the system may include a light source 102 for generating a brightfield incident beam, such as a broadband light source. Examples of brightfield light sources include a laser-driven light source, a high-power plasma light source, a transillumination light source (e.g., halogen lamp), a filtered lamp, LED light source, etc. The inspection system may include any suitable number and type of light sources.

The incident beam from the light source then passes through a number of lenses which serve to relay (e.g., shape, focus or adjust focus offset, filter/select wavelengths, filter/select polarization states, resize, magnify, reduce distortion, etc.) the beam towards a sample 116. In the illustrated embodiment, the incident beam passes through lens 104, which collimates the incident beam, and then through lens 106, which converges the incident beam. The incident beam is then received by beam splitter 112 that then reflects the incident beam through objective lens 114, which focuses the incident beam onto sample 116 at one or more incident angles.

The sample 116 may also be placed on a stage (not labeled) of the inspection system 100, and the inspection system 100 may also include a positioning mechanism for moving the stage (and sample) relative to the incident beam. By way of examples, one or more motor mechanisms may each be formed from a screw drive and stepper motor, linear drive with feedback position, or band actuator and stepper motor. The one or more positioning mechanisms may also be configured to move other components of the inspection system, such as the illumination or collection aperture selector, wavelength filters, input or output polarization filters, etc.

The inspection system 100 may also include an illumination selector 105 positioned at a pupil plane of the illumination beam. In one embodiment, the illumination selector 105 is in the form of a configurable pupil aperture that is adjustable to produce a plurality of different illumination beam profiles at the pupil plane. In a specific implementation, the illumination selector 105 can produce more than 25 different beam profiles. In yet another implementation, the illumination selector 105 can produce more than 100 different beam profiles. The inspection system 100 may also include one or more positioning mechanisms for selectively moving the different aperture configurations of the illumination selector into the path of the incident beam.

Figure 2:
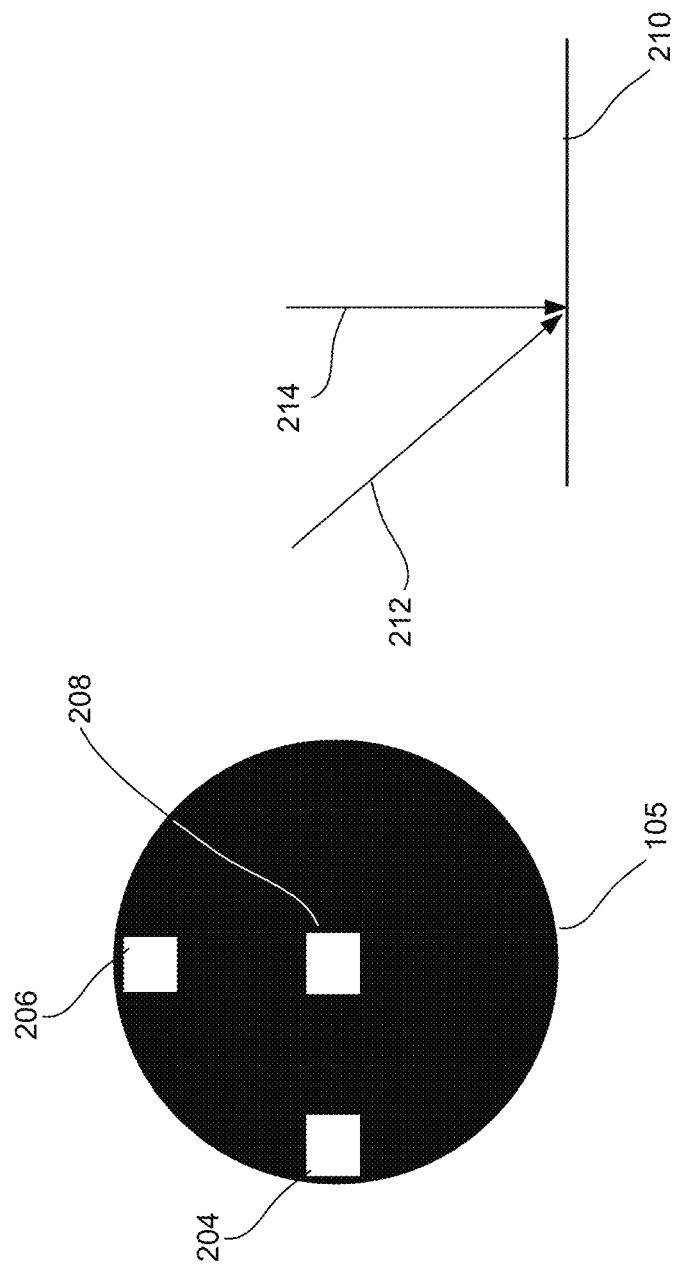
FIG. 2 illustrates different aperture configurations with respect to the incident beam's pupil that result in different incident angles.

In general, different illumination beam profile or aperture configurations result in different incident beam angles on the sample as described further herein. FIG. 2 illustrates different aperture configurations with respect to the incident beam's pupil 105 that result in different incident angles with respect to the sample plane for the incident beam impinging on a sample 210. Apertures closer to the center of the incident beam's pupil area result in larger incident angles on the sample, as compared with apertures that are positioned closer to the periphery of the incident beam's pupil area. For example, a center aperture 208 results in an incident beam 214 with a normal incident angle, while an outer aperture (204) results in an incident beam with a higher (or oblique) incident angle, such as 212.

After the incident beam(s) impinge on the sample 116, the light may then be reflected (and/or transmitted) and scattered from the sample 116, which is referred to herein as "output light" or an "output beam." The inspection system also includes any suitable lens arrangements for directing the output light towards one or more detectors. In the illustrated embodiment, the output light passes through beam splitter 112, Fourier plane relay lens 120, imaging aperture 122, and zoom lens 124. The Fourier plane relay lens 120 generally relays the Fourier plane of the sample to the imaging aperture 122. The imaging aperture 122 may be configured to block portions of the output beams. For instance, the aperture 122 is configured to pass all of the output light within the objective numerical aperture in a bright field inspection mode, and configured to pass only the scattered light from the sample during a dark field inspection mode. A filter may also be placed at the imaging aperture 122 to block higher orders of the output beams so as to filter periodic structures from the detected signal.

After going through the imaging aperture 122, the output beam may then pass through zoom lens 124, which serves to magnify the image of the sample 116. The output beam then impinges upon detector 126. By way of example, the detector may be in the form of a CCD (charge coupled device) or TDI (time delay integration) detector, photomultiplier tube (PMT), or other sensor.

The illumination side may also include any suitable mechanisms for selecting spectral band and input and polarization states. For instance, the system 100 may include a plurality of color or wavelength filters 130 for selecting different wavelength ranges, and an input polarizer 132 for selecting different input polarization states. Likewise, the collection side may include an output polarizer 134 for selecting different polarization states.

The signals captured by the sensor 126 can be processed by a controller or computer system 110, which may include a signal processing device having an analog-to-digital converter configured to convert analog signals from the sensor into digital signals for processing. The controller 110 may be configured to analyze intensity, phase, and/or other characteristics of the sensed light beam. The controller 110 may be configured (e.g., with programming instructions) to provide a user interface (e.g., on a computer screen) for displaying resultant test images and other inspection characteristics as described further herein. The controller 110 may also include one or more input devices (e.g., a keyboard, mouse, joystick) for providing user input, such as changing aperture configuration, viewing detection results data or images, setting up a inspection tool recipe. In certain embodiments, the controller 110 is configured to carry out aperture or mode optimization techniques and inspection processes. Techniques of the present invention may be implemented in any suitable combination of hardware and/or software. The controller 110 typically has one or more processors coupled to input/output ports, and one or more memories via appropriate buses or other communication mechanisms.

The controller 110 may be any suitable combination of software and hardware and is generally configured to control various components of the inspection system 100. For instance, the controller may control selective activation of the illumination sources 102, the illumination selector/aperture 105 settings, the imaging aperture 122 settings, wavelength band, focus offset setting, polarity settings, etc. The controller 110 may also be configured to receive the image or signal generated by the detector 126 and analyze the resulting image or signal to determine optimum aperture configurations or whether defects are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

It should be noted that the above description and drawings are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

In general, certain embodiments of the present invention provide a technique to quickly and comprehensively review different illumination and/or collection aperture configurations (and corresponding different incident angles) or modes on an inspection tool. The following example embodiments pertain to illumination aperture configurations in the pupil area. However, the following techniques can readily be applied to collection aperture configurations in the Fourier plane area.

Conceptually, the illumination pupil area can be divided into a plurality of positions and an illumination aperture may be opened one at a time for each pupil position. The pupil positions can be selected so that the variance of defect detection performance across the pupil can be determined. The pupil positions and corresponding apertures can be spread across the entire pupil so as to provide full angular coverage for the incident beam impinging on the sample. The pupil positions and corresponding apertures can have a relatively high density with respect to the pupil area. In a specific implementation, the pupil is divided into 40 grid points. In another implementation, the number of pupil positions is greater than 100 grid points. In yet another implementation, the number of pupil positions is greater than 200 grid points. Said in another way, the resolution of the illumination aperture per grid can be higher with higher grid sampling.

The different aperture settings can be independent of each other. For instance, the illumination beam is incoherent. In one embodiment, the aperture configurations are positioned at different pupil locations that are unique and do not overlap so as to result in different angles of incidence. In another embodiment, some of the selected aperture configurations can depend on each other and have overlapping pupil locations.

In one embodiment, image data obtained for each independent pupil location may be used to determine an optimum aperture setting. The image data may be obtained by imaging known defect areas using different independent apertures one at a time or by simulating defect images for a particular defect type with each aperture opened individually on a particular inspection tool. In the simulation embodiment, a defect on a sample and the inspection tool optics, including individual apertures being opened one at a time, are simulated, for example, by an optical tool model. The model may include a Jones scattering matrix for representing the angular and polarization scattering properties of the media and embedded defect.

Figure 3:
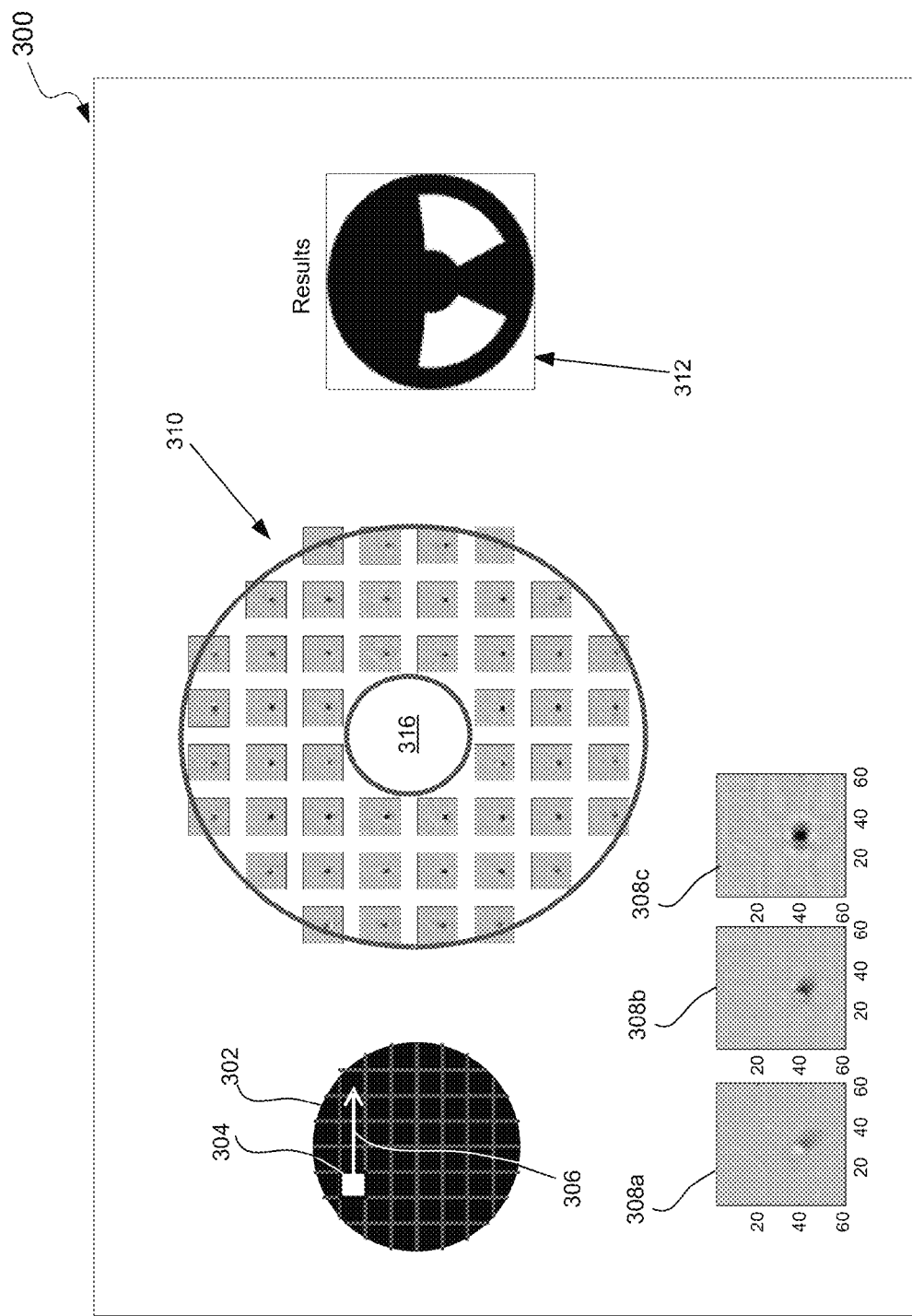
FIG. 3 illustrates a process for automatically finding an optimum aperture based on defect images obtained with an inspection tool using a set of base aperture apertures in accordance with one embodiment of the present invention.

Each defect image may be obtained by for any suitable shape and number of "base" apertures. FIG. 3 illustrates a process for automatically finding an optimum aperture based on defect images obtained with an inspection tool using a set of base aperture apertures in accordance with one embodiment of the present invention. In this example, the base apertures are in the form of square or rectangular shapes that are spread across the pupil area. As shown, pupil aperture element 302 shows a current aperture position 304 with respect to the illumination pupil as the aperture position moves across the pupil, for example, in direction 306. For instance, a known defect area may be imaged with the inspection tool for a plurality of sequential aperture positions across a substantial portion of the pupil. A plurality of known defect areas, for example, having different defects groups may also be imaged at each aperture position.

As each pupil aperture is individually opened, a GUI may also be displayed to a user and provide a detection graphical element 310 that maps each pupil position to particular detection results obtained from the inspection tool For instance, the detection graphical element 310 includes images that are arranged with respect to each other in the same way that the corresponding pupil aperture positions are arranged with each other. The detection graphical element 310 may also include an unobserved area 316 that corresponds to a particular pupil area from which detection results are not desired. For instance, the unobserved area 316 corresponds to a central portion of the pupil for which apertures were not applied potentially because of additional hardware blockage in the system.

As an aperture may be opened at each pupil position, a smaller subset of corresponding thumbnails may be provided. As shown, the GUI 300 may also be configured to provide a thumbnail image that corresponds to the current pupil position (308c), in addition to the most recently obtained thumbnail images (308a and 308b). This arrangement may be configured to allow a user to review each defect image. Additionally, certain embodiments of the present invention also pertain to automated processes for reviewing each image, as well as each set of combined images, as described further herein.

Figure 4A:
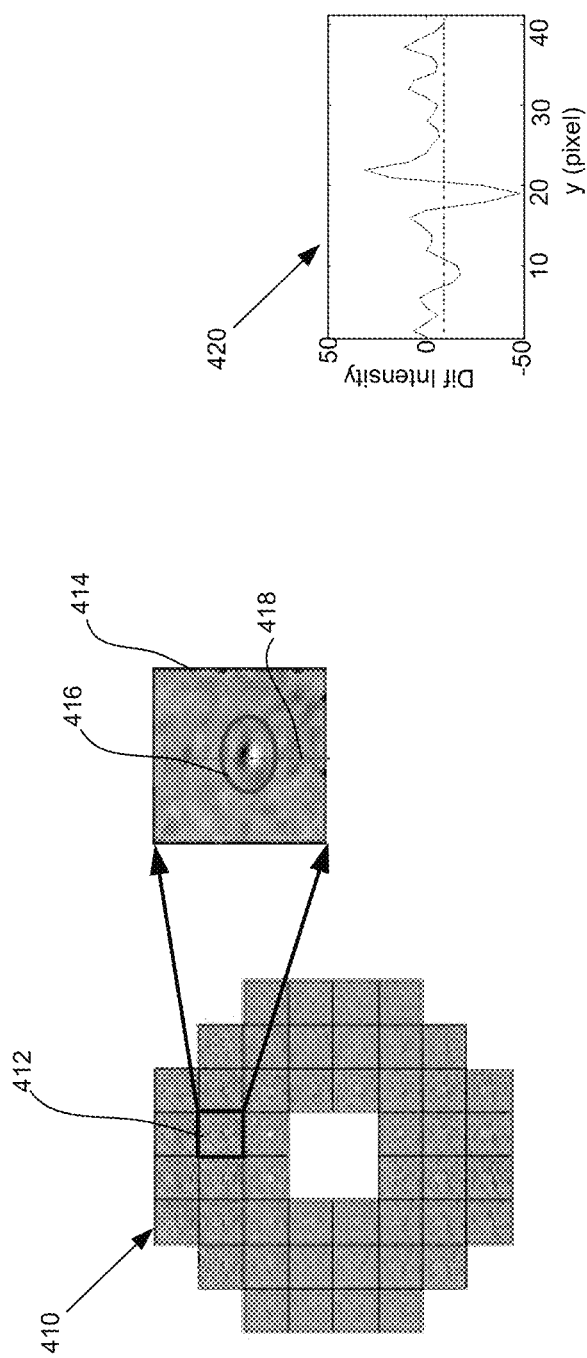
FIG. 4A illustrates a defect detection characteristic for a particular pupil aperture position in accordance with a specific implementation of the present invention.

FIG. 4A illustrates a defect detection characteristic for a particular pupil aperture position in accordance with a specific implementation of the present invention. As shown, an image 414 of a defect area that includes defect 416 may be either obtained for a particular aperture position 412 of the illumination pupil 410 using an inspection system or an inspection system model. For instance, graph 420 shows example intensity values of the image as a function of sample position within the imaged or simulated defect area for the particular aperture position.

Once an image is obtained for each of the aperture positions, these detected or simulated detection images or signals may be analyzed individually and in combination to determine an aperture configuration that provides optimum defect detection results. For instance, the set of one or more individual apertures that result in the highest contrast for a defect (or a plurality of defects) may be selected. An example optimum aperture configuration 312 is shown in FIG. 3. In general, the quality of the defect detection characteristic may be based on the contrast between the intensity peaks and background intensity values (see graph 420).

Figure 4B:
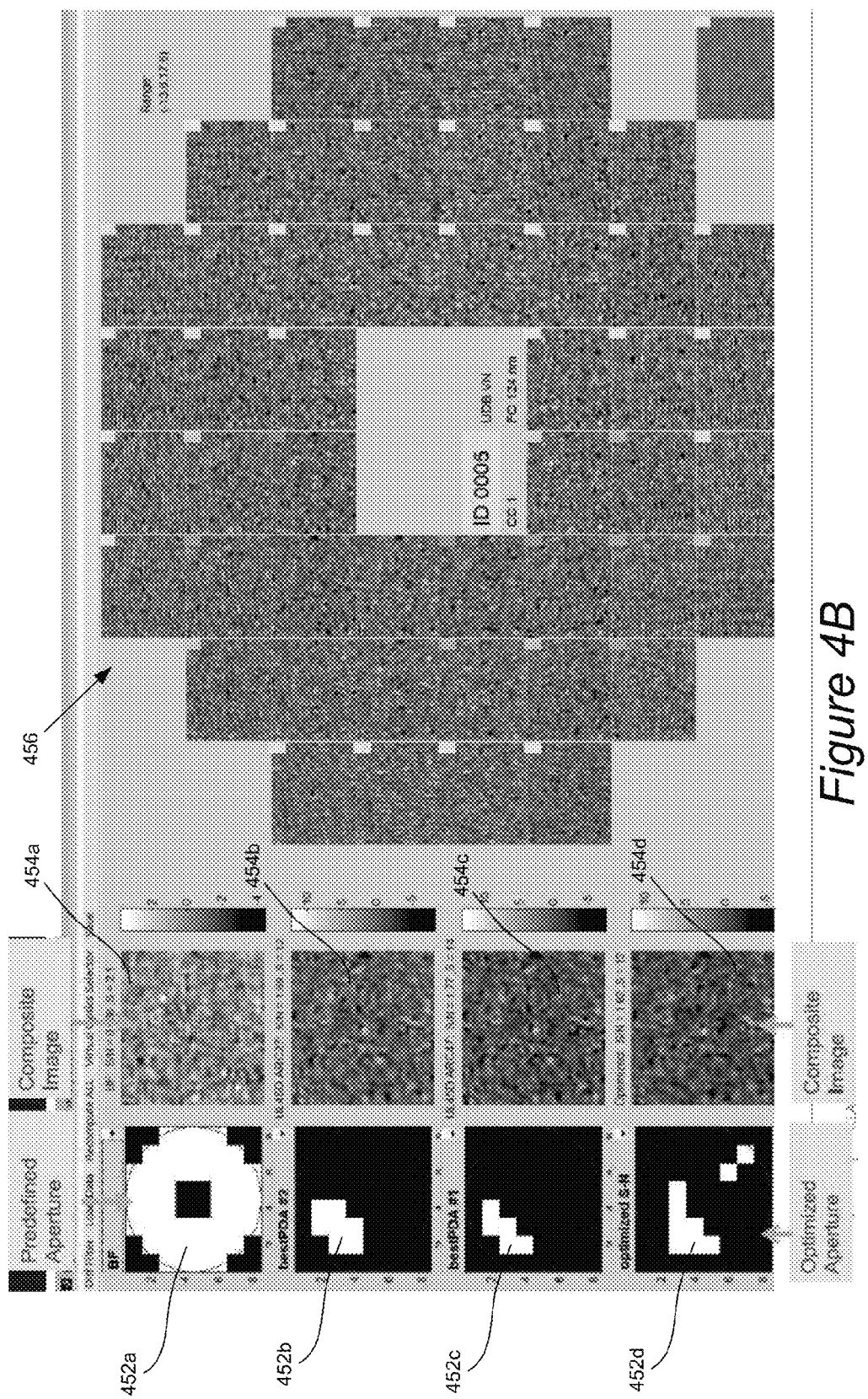
FIG. 4B illustrates selection of an optimum set of base apertures by combining images that were obtained for individual apertures in accordance with one embodiment of the present invention.

FIG. 4B illustrates selection of an optimum set of base apertures by combining images that were obtained for individual apertures in accordance with one embodiment of the present invention. As shown, a plurality of images 456 may be obtained for each aperture position with an inspection tool having an aperture selector or with a simulation model. Various combinations of these individual images 456 may be automatically summed together to form composite images for different aperture combinations. As shown, composite images 454a, 454b, 454c, and 454d are generated for aperture combinations 452a, 452b, 452c, and 452d, respectively. Of course, composite images may be obtained for other aperture combinations.

A composite image may be obtained for all aperture combinations that are possible or for a predefined set of aperture combinations. For example, the predefined aperture combinations may include aperture configurations that are estimated to provide the most optimal defect detection results, while exclude aperture configurations that are unlikely provide optimal defect detection results. As shown, aperture combination 452a is a bright field configuration in which all (or most) of the available apertures are opened. Aperture combinations 452b-452d block part of the apertures while leaving a subset of the apertures open.

A defect detection characteristic for each composite image may be analyzed to determine an optimum aperture combination as described further herein. One example of a defect detection characteristic is a signal to noise (S/N) ratio. Other examples include a difference between a signal and noise signal, etc. In the illustrated example, composite image 454c for combined apertures 452c has a S/N ratio of 1.77, while composite image 454d for aperture combination 452d has a S/N ratio of 1.92. If aperture combination 454d has the highest S/N ratio of all of the aperture combinations or all of a predefined set of aperture combinations, such aperture combination 54d can be defined as the optimum aperture configuration. Other metrics may be used to define an optimum aperture combination as described further herein.

For each aperture combination, a composite image may be generated from the actual images that were obtained as experimental data (or simulated) for each individual aperture position. The defect position in the composite image may optically shift based on different illumination angles from different aperture configurations, for example. Accordingly, each point in a region of interest (ROI) may be analyzed for signal strength/intensity, as compared to a noise signal strength value (e.g., average of signal outside ROI). For example, a ROI may have 400 points to analyze for each aperture combination. The point and aperture combination that results in the best S/N ratio or S-N difference may be defined as the defect and best aperture configuration.

Figure 5:
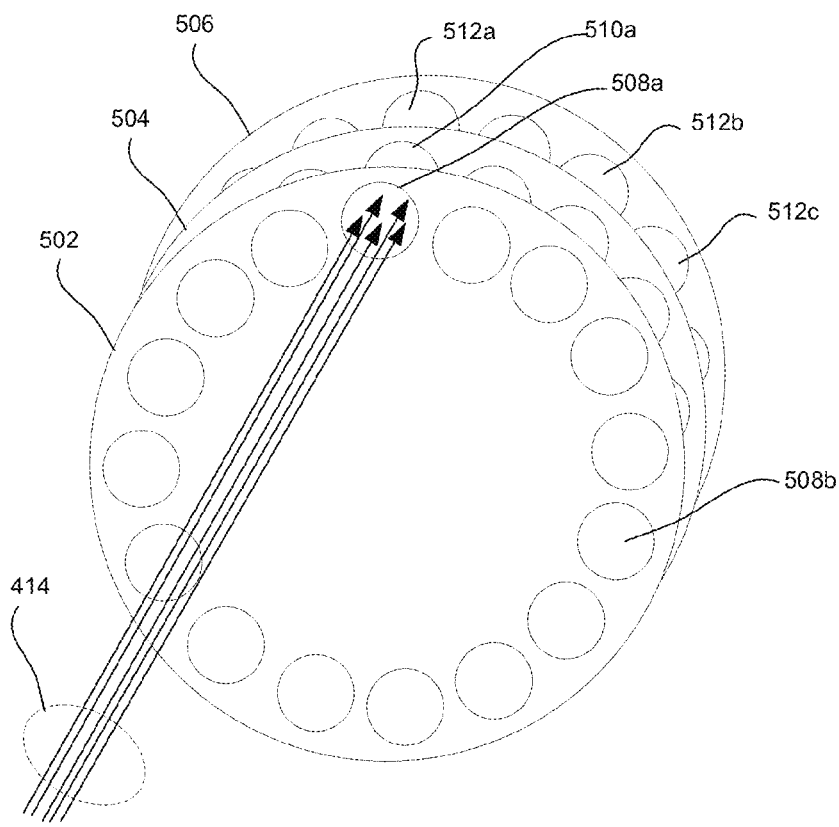
FIG. 5 is diagrammatic perspective view of an illumination selector in accordance with one embodiment of the present invention.

Before describing further aperture (and mode) selection techniques, embodiments of an aperture selector will first be described. An illumination (or collection) aperture selector for selectively applying an aperture to each of a plurality of pupil (or Fourier plane) positions or configuring an optimum aperture configuration may take any suitable form. FIG. 5 is diagrammatic perspective view of an illumination selector in accordance with one embodiment of the present invention. In this example, the illumination selector comprises three apertures disks 502, 504, and 506. Each aperture disk includes a plurality of different aperture configurations (e.g., aperture configurations 508a and 508b for disk 502, aperture configuration 510a for disk 504, and aperture configurations 512a, 512b, and 512c for disk 506). A particular aperture configuration for receiving the incident beam (or ray bundles) 414 can be selected for each disk and then the three selected aperture configurations from the three disks can then be overlaid to result in a diverse number of aperture settings and resulting illumination pupil profiles. After an optimum aperture configuration is found using any of the techniques described herein, the three aperture disks can be moved with respect to each other to achieve the optimum aperture configuration (if available) for the illumination (or collection) beam.

Each aperture configuration of each disk may include at least one transparent portion and may also include one or more opaque regions. For example, the transparent portions can be formed from any suitable transparent materials, such as glass, quartz, fused silica, etc., or each transparent region can merely be devoid of material so that light passes through each transparent portion of the aperture configuration. In contrast, each opaque portion blocks the corresponding spatial portion of the incident beam at the pupil plane, and each opaque portion is generally formed from an opaque material, such as chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material. The shape of each aperture's transparent portion may be any suitable shape, such as rectangular, circular, elliptical, an lhcscreen (superposition of a circle and rectangle), marguerite (two lhcscreens, one rotated by 90°), rectellipse (superposition of an ellipse and rectangle), racetrack, etc. In general, an aperture configuration produces a particular incident beam profile, such as dipole, quadrapole, quasar, annulus, etc. In a specific example, Source Mask Optimization (SMO) or any pixelated illumination technique may be implemented. In the illustrated embodiment, each aperture configuration covers the entire illumination pupil area and is centered on the optical axis. However, an aperture configuration may alternatively be placed in a portion of the pupil area or at some other point (not pupil plane) along the optical path of the incident beam. MEMS mirror arrays can be used to form reflective programmable apertures as an alternative to blocking multidisc apertures. In alternative embodiments, reflective mirror type aperture configurations, which are formed from an opaque mask patterned over a reflective mirror substrate, may be used in reflected illumination (or collection) beam systems or combination transmission and reflective type systems.

Figure 6A:
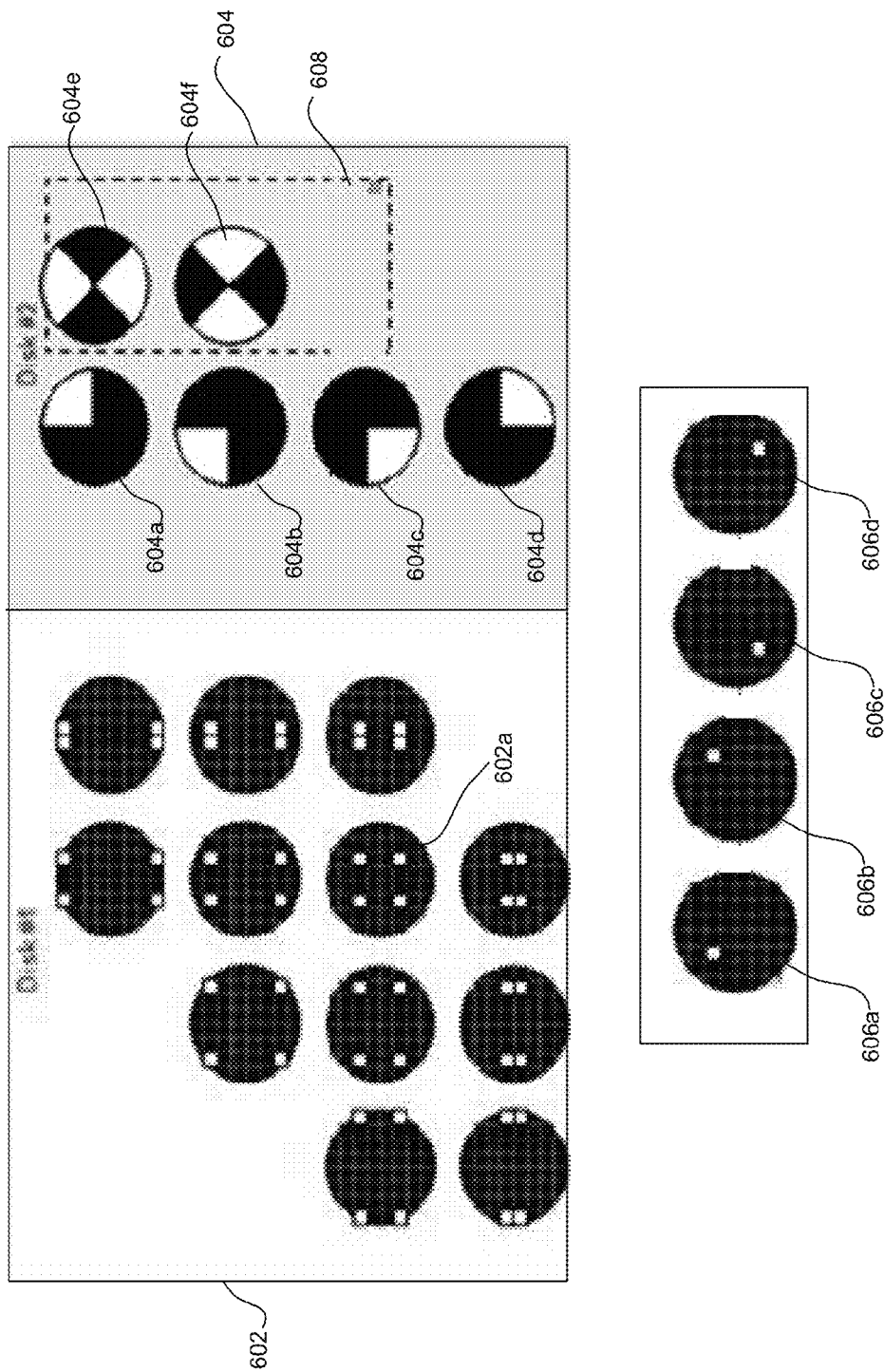
FIG. 6A illustrates combining individual apertures to achieve different aperture configurations in accordance with a specific example implementation of the present invention.

FIG. 6A illustrates combining individual apertures to achieve different aperture configurations in accordance with a specific example implementation of the present invention. As shown, a particular aperture configuration 602a of a first disk 602 can be combined with one of four aperture configurations 604a, 604b, 604c, and 604d of a second disk 604. The four different combinations would result in aperture configurations 606a~606d. For instance, combining aperture configuration 602a from disk 602 with aperture 604a of disk 604 results in aperture configuration 606b. Likewise, combining aperture configuration 602a from disk 602 with aperture 604b of disk 604a. The illumination selector may include other aperture configurations on each disk (e.g., 604e and 604f) that may be combined with other aperture configurations from other disks for achieving an optimum set of apertures.

A subset of the available different aperture configurations can be utilized in any suitable manner, such as finding one or more optimum configurations that are also available on the inspection tool, as well as finding and designing one or more optimum aperture configurations that are not available on the tool. In a specific embodiment, the results for the subset of individual aperture positions serve as a basis set that can be used to estimate the results for combined aperture positions from which an optimum aperture configuration is found.

Figure 6B:
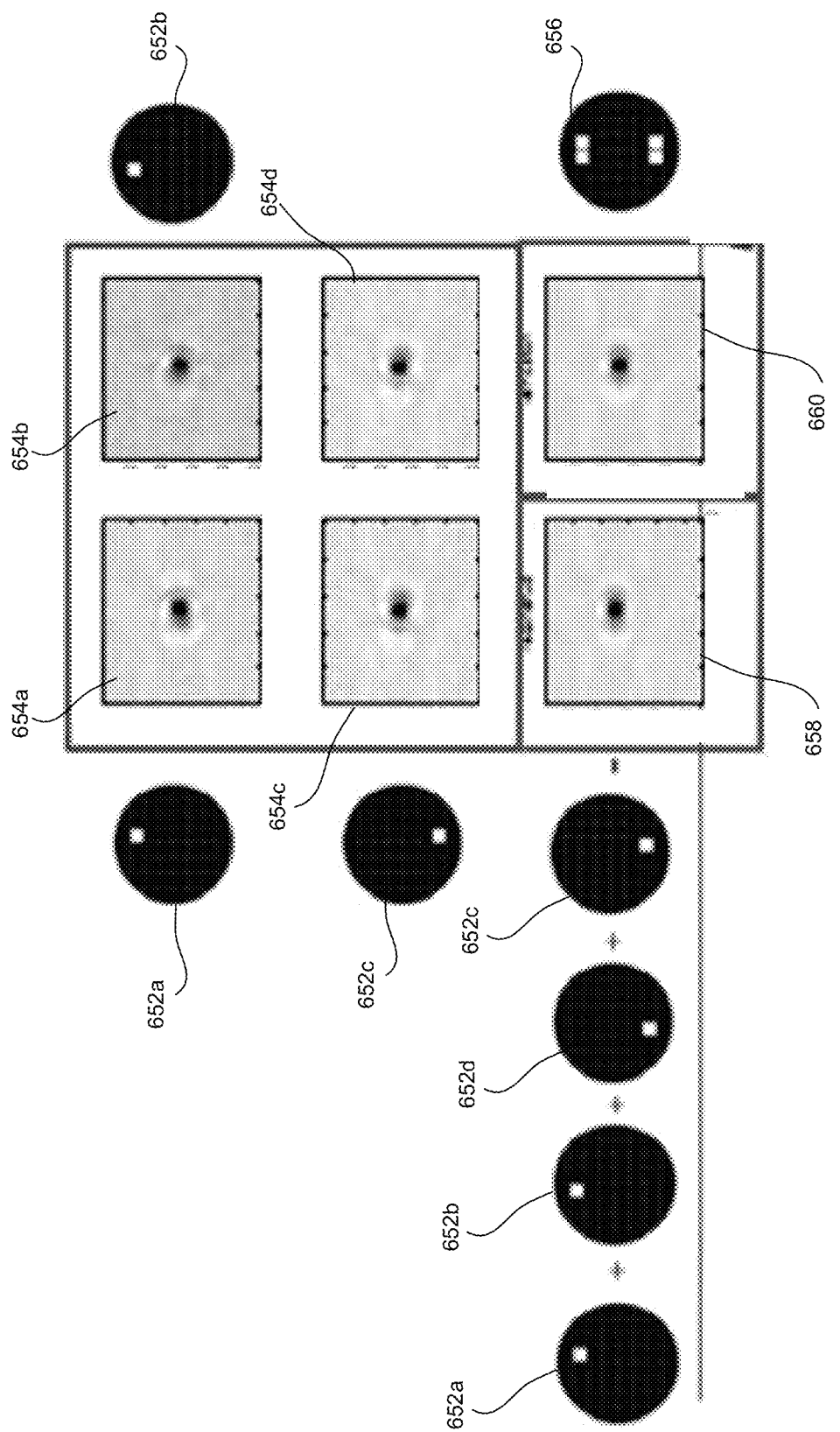
FIG. 6B illustrates a process for generating a composite image for multiple aperture positions based on images obtained using a basis set of individual apertures of an inspection tool in accordance with a specific example.

FIG. 6B illustrates a process for generating a composite image for multiple aperture positions based on images obtained using a basis set of individual apertures of an inspection tool in accordance with a specific example. For instance, four different images may be detected for an aperture placed at four different pupil positions. As shown, aperture configuration 652a results in image 654a; aperture configuration 652b results in image 654b; aperture configuration 652c results in image 654c; and aperture configuration 652d results in image 654d. Each aperture configuration has a single aperture at a single position and the light passing through each aperture is incoherent so the individual apertures are independent from each other.

The resulting images can be combined to generate an image for apertures being opened at all four positions. Specifically, images 452a~452d that resulted from aperture configurations 652a~652d are added together to obtain a composite image 658 for an aperture configuration having apertures at all four aperture positions (e.g., combination of 652a~652d). That is, image 658 is a reconstructed image or an estimate of the results that would occur with an aperture configuration 656. If the aperture configuration 656 is determined to be the optimum aperture configuration and such aperture configuration is available on the inspection tool, for example, by selecting and overlaying different aperture configurations (e.g., from different disks) of the illumination selector, this aperture configuration can be used to form an actual image 660, which can be verified as producing optimal results. Otherwise, a new aperture configuration can be fabricated and verified.

The aperture settings that are used to collect results from the inspection tool may also generally be used as a basis set for estimating results for additional aperture settings that are not currently available on the inspection tool. The estimation of results for a non-existing aperture setting can be determined without additional data collection or input, but simply based on the results from the basis set of aperture settings that are available on the inspection tool.

Figure 7:
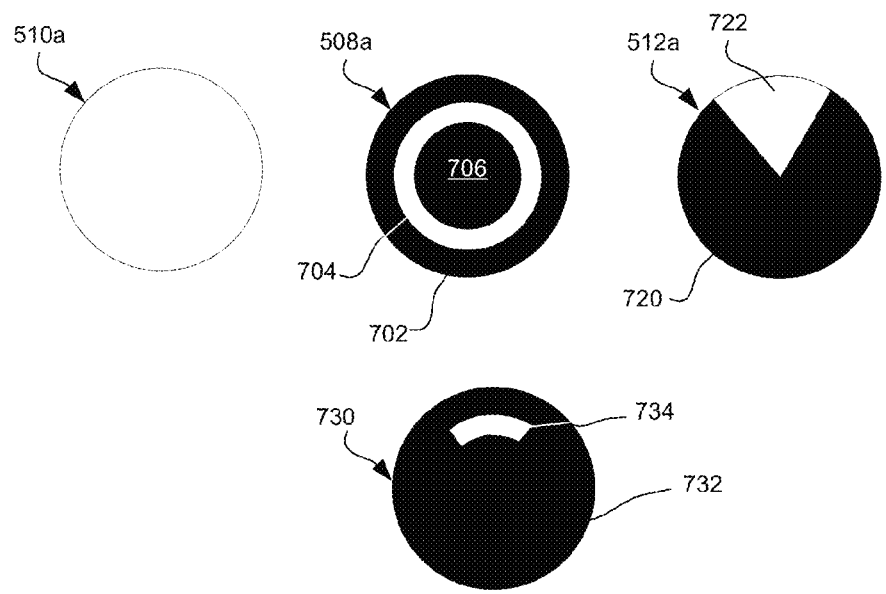
FIG. 7 illustrates combining three aperture configurations to achieve a first example of an aperture configuration.

The following examples illustrate only a small subportion of the diverse number of aperture configurations that may be achieved with certain embodiments of the present invention. FIG. 7 illustrates combining three aperture configurations to achieve a first example of an aperture configuration. As shown, a first aperture configuration 510a selected from a first disk (504 of FIG. 5), a second aperture configuration 508a of a second disk (502), and a third aperture configuration 512a of a third disk (506) may be overlaid and combined to achieve a final aperture configuration 730 through which the illumination or incident beam (414) is passed, for example, at the pupil plane.

The first aperture configuration 510a does not include any blocking or opaque portions and, accordingly, lets the entire pupil area transmit ray bundles from the illumination beam. That is, all of the ray bundles in the pupil area pass through the first aperture 510a. The second aperture configuration 508a has an inner transparent ring 704, a center opaque portion 706, and an outer ring opaque portion 702. The third aperture configuration 512a has a transparent wedge portion 722 and an opaque portion 720 for the other wedges of pupil area. The resulting aperture configuration 730 has a transparent arc segment 734 that is surrounded by opaque portion 732.

Figure 8:
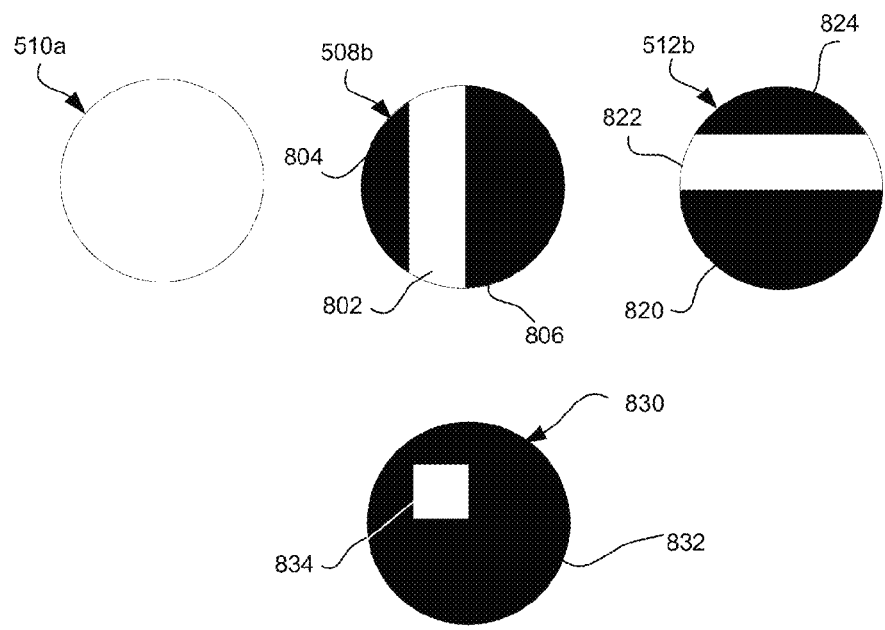
FIG. 8 illustrates combining three aperture configurations to achieve a second example of an aperture configuration.

FIG. 8 illustrates combining three aperture configurations to achieve a second example of an aperture configuration. Like FIG. 7, the first aperture configuration 510a is totally transparent over the entire pupil area. The second aperture configuration 508b of FIG. 8 has a transparent vertical transparent strip 802 surrounded by opaque portions 804 and 806. The third aperture configuration 512b has a horizontal transparent strip 822 surrounded by opaque portions 824 and 820. The resulting aperture configuration 830 has a square transparent portion 834 surrounded by opaque portion 832.

Figure 9:
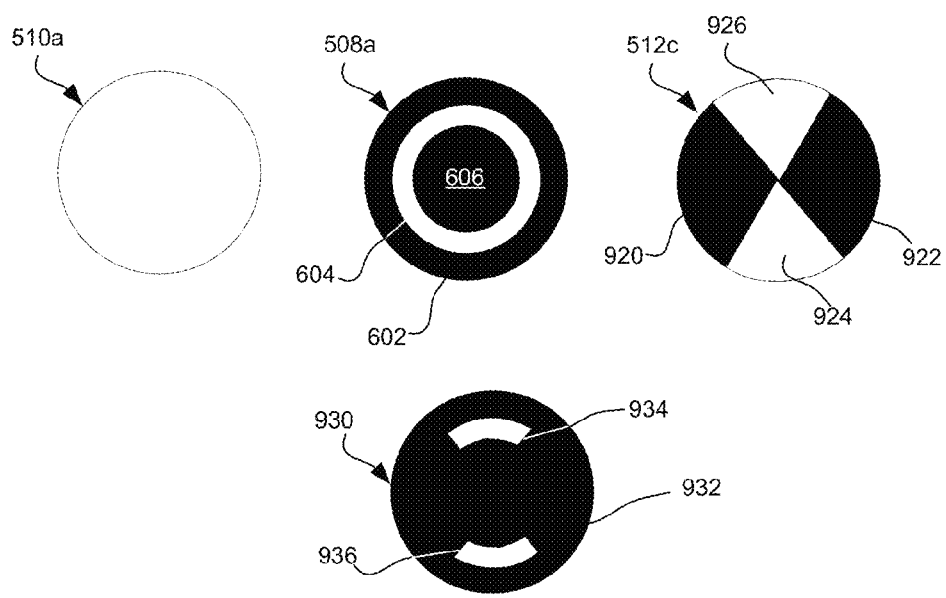
FIG. 9 illustrates combining three aperture configurations to achieve a third example of an aperture configuration.

FIG. 9 illustrates combining three aperture configurations to achieve a third example of an aperture configuration. The first aperture configuration 510a is totally transparent and the second aperture configuration 508a is identical to the aperture 508a of FIG. 7. The third aperture configuration 512c has transparent wedge portions 924 and 926 and opaque wedge portions 920 and 922. The resulting aperture configuration 930 has transparent arc segments 934 and 936 surrounded by opaque portion 932.

In an alternative embodiment, the illumination pupil (or collection Fourier) profile may be dynamically configured using a fiber bundle so as to determine an optimum profile configuration. Several embodiments of such an apparatus are further described in U.S. Pat. No. 7,319,229, issued 15 Jan. 2008, by Vaez-Iravani et al., which patent is incorporated herein by reference in its entirety. In one aspect, an illumination profile apparatus may include a plurality of optical fibers for receiving one or more incident beam(s) and outputting such beam(s), a lens arrangement for receiving the beam(s) and directing the beam(s) towards a sample, and an illumination selector for transmitting one or more incident beams on selected ones of the fibers. In other words, different numbers of fibers may be selected to transmit different numbers of incident beams at different incident angles towards the sample. In other embodiments, the illumination pupil (or collection Fourier) profile may be configured using a programmable aperture.

Figure 10:
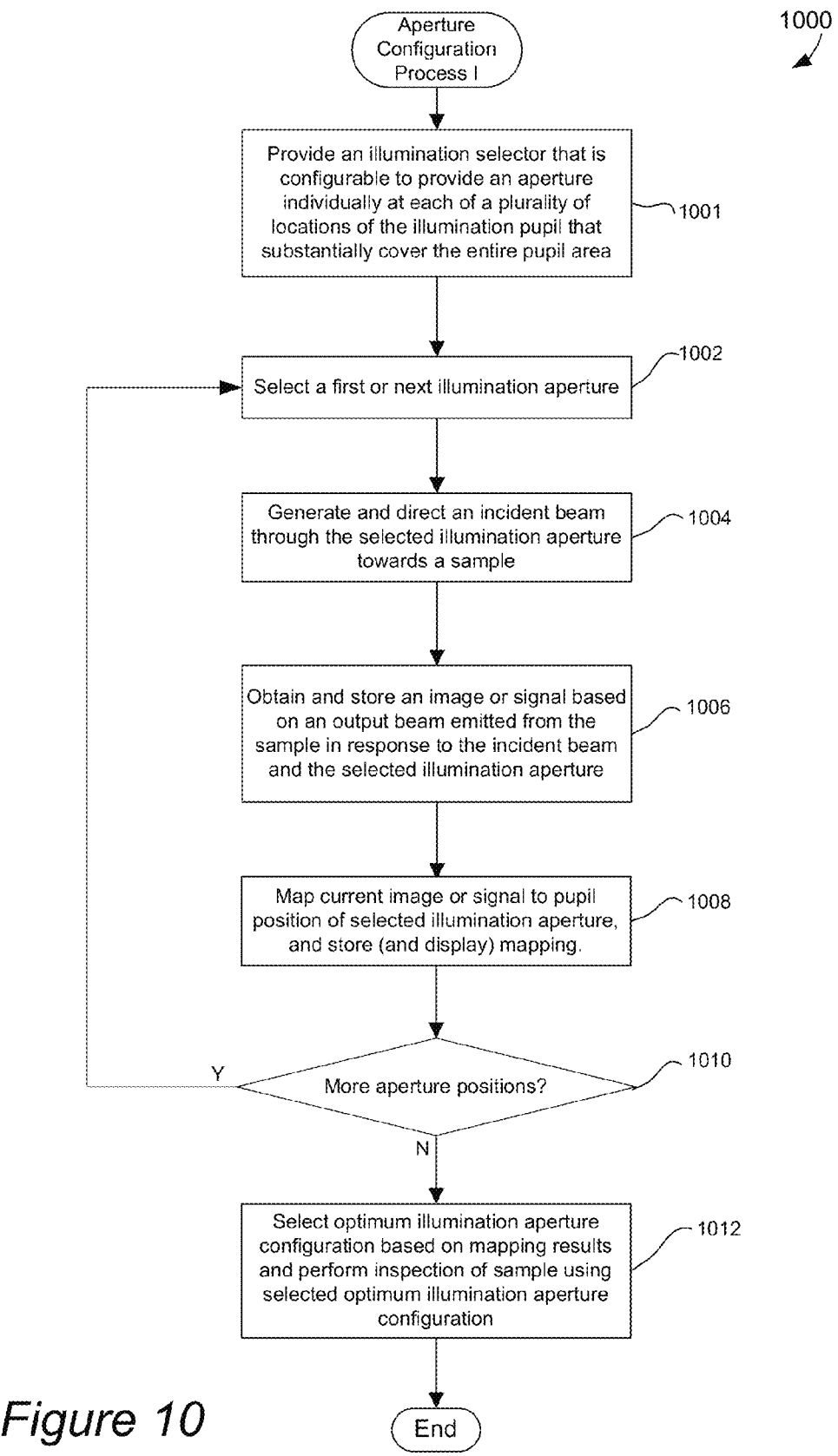
FIG. 10 is a flow chart illustrating a procedure for finding an optimum aperture configuration using images obtained with an aperture selector on an inspection tool in accordance with one embodiment of the present invention.

In certain embodiments, a basis set of aperture configurations can be used to test each aperture position with respect to the pupil or Fourier plane and then determine an optimum aperture configuration. Any suitable technique may be used to accomplish this goal. FIG. 10 is a flow chart illustrating a procedure 1000 for finding an optimum aperture configuration using images obtained with an aperture selector on an inspection tool in accordance with one embodiment of the present invention. This example process uses an illumination aperture selector (e.g., FIG. 5) at a pupil plane to obtain experimental data for illumination side apertures although other planes could be used, for example, for obtaining experimental data for collection side apertures.

As shown, an aperture selector that is configurable to provide an aperture individually at each of a plurality of locations of the illumination pupil is provided in operation 1001. In a specific implementation, the pupil locations substantially cover the entire pupil area.

A first one of the illumination apertures is selected in operation 1002. For instance, the illumination selector is configured so as to place an aperture at a first grid point of a pupil area that has been divided into an array of grid point locations that substantially cover the pupil area. An aperture configuration can be selected on each of the illumination selector's disks and the selected aperture configurations from the different disks are moved to be positioned within the pupil area and perpendicular to the optical axis of the incident beam.

An incident beam is then generated and directed through the selected illumination aperture towards the sample in operation 1004. For instance, the selected aperture position results in a ray bundle being transmitted towards the sample at one or more first angles of incident. The selected aperture results in the incident beam may be directed towards the sample at a single incident angle or at a narrow range of incident angles, e.g., each selected aperture position can correspond to less than about 5 degrees of angles of incident. The sample may include any number and type of defects of interest (DOI's), nuisance defects, and noise.

In a specific example, different aperture configurations may be selected from different disks of the illumination selector, and these selected aperture configurations have different opaque and transparent portions in the pupil area. The selected aperture configurations can be overlaid with each other to cause a single aperture to be positioned at a particular grid point of the illumination pupil plane so that most of the incident beam is blocked going through the pupil area, except for a ray bundle corresponding to the single aperture at the particular grid point. The resulting incident beam will have an incident angle corresponding to the particular grid point of the pupil area. For example, if the aperture is placed as the outer edge of the pupil area, the incident beam will have a relatively oblique angle (e.g., see FIG. 2).

An image or signal may then be obtained and stored based on an output beam emitted from the sample in response to the incident beam and the selected illumination aperture in operation 1006. An image or signal of a known defect area may be obtained and stored for an independent aperture being opened at each of a plurality of aperture positions that are substantially spread across a pupil area or substantially cover a pupil area, possible excluding a center region. By way of specific example, each image or signal can pertain to defect-of-interest (DOI) signal strength, noise signal strength, and nuisance defect signal strength. Each signal strength value may take the form of one or more of the following values pertaining to a real defect, nuisance defect, or noise: intensity value, image texture value, polarity (e.g., whether the defect or background flips from negative to positive values), etc. Any of the image or signals characteristics described herein can pertain to an actual DOI defect, nuisance defect, or difference signal/image between the defect and a reference sample area.

The image or signal for each aperture position can be obtained with respect to a known defect area having a defect portion and nuisance or background portion. Any suitable technique can be used to define one or more defect area (e.g., region of interest) on the sample, such as a wafer. For example, a user can define defect, nuisance, and/or noise sites on the sample. The background areas can be defined as areas that have not been determined to be defects.

The current image or signal may then be mapped to the pupil position of the selected illumination aperture and this mapping stored in operation 1008. The image or signal may also be displayed in association with the corresponding aperture position for the operator of the inspection tool (e.g., FIG. 3). The pupil position at which the current aperture is positioned may be mapped with the resulting image and/or signal value for a particular DOI or set of DOI's (or nuisance or noise). The mapping can be stored and/or displayed in any suitable manner so as to associate aperture position with a resulting defect detection characteristic, such as a DOI (or nuisance or noise) image or signal. Alternatively, the mapping between all of the aperture positions of the pupil area and their corresponding image or signal can be displayed after the images and signals are detected and collected by the inspection tool for all aperture positions or not at all.

After mapping is obtained for the current aperture position, it may then be determined whether there are any more aperture positions in operation 1010. For instance, the operations for obtaining images (or signals) may be repeated for each grid point of the illumination pupil area. For each aperture position, the image or signal is collected from each sample target with the sample stage position being substantially fixed and minimizing camera image vibration so that the image misalignment between different illumination directions is negligible (close to zero). For instance, image/signal data is collected for each aperture position by using an illumination aperture selector and for each band by swapping color (wavelength) filters. Camera vibration may be maintained at a setting equal to or below ½ of cameral pixel (e.g., ½ of a 50 nm pixel corresponds to a 25 nm vibration limit). Stage motion or vibration may be compensated by image alignment using recorded stage coordinates.

After the images and defect detection characteristic data has been collected for each pupil position in the illustrated embodiment, an optimum illumination aperture configuration may then be selected based on the mapping results in operation 1012. An optimum aperture configuration may be found by analyzing all of the collected images or signals for each of the basis aperture positions, as well as all combinations of such basis aperture positions. For example, an aperture configuration that results (or is estimated to result) in a maximum DOI signal to noise ratio (SNR) value or a maximum DOI signal to nuisance defect ratio value may be selected as an optimum aperture configuration. An inspection of the sample may then be performed using the selected optimum illumination aperture configuration in operation 1012.

In an automated embodiment, detected images or signals can be added together for each combination of one or more illumination aperture positions and composite images or signals can then be used to determine an optimum aperture configuration. The combination that has an optimum combined result can then be defined as the optimum aperture configuration. For instance, image data for each aperture combination (from different incident angles) is added together to form a composite image. Signal strength for each aperture combination can also be added together. Other types of image metrics, such as image texture, polarity, etc., can also be added together.

Each set of summed images or signals can be analyzed to determine a defect metric and nuisance/noise metric. It may then be determined which combination of apertures results in a maximized defect metric and a minimized nuisance or noise metric.

Alternatively, simulated images or signals (as opposed to real images or signals obtained from an experimental wafer) for each aperture position may be combined into different composite images to determine an optimum aperture configuration.

Certain embodiments provide an efficient way to determine an optimum aperture setting for an inspection tool. Certain embodiments of the present invention may also provide an aid to better understand DOI, nuisance, and background characteristics as a function of illumination angle. Additionally, detect characteristic data can be used as an engineering diagnostic tool to evaluate the optical performance across different illumination angles to provide solutions for tool matching problems.

Figure 11B:
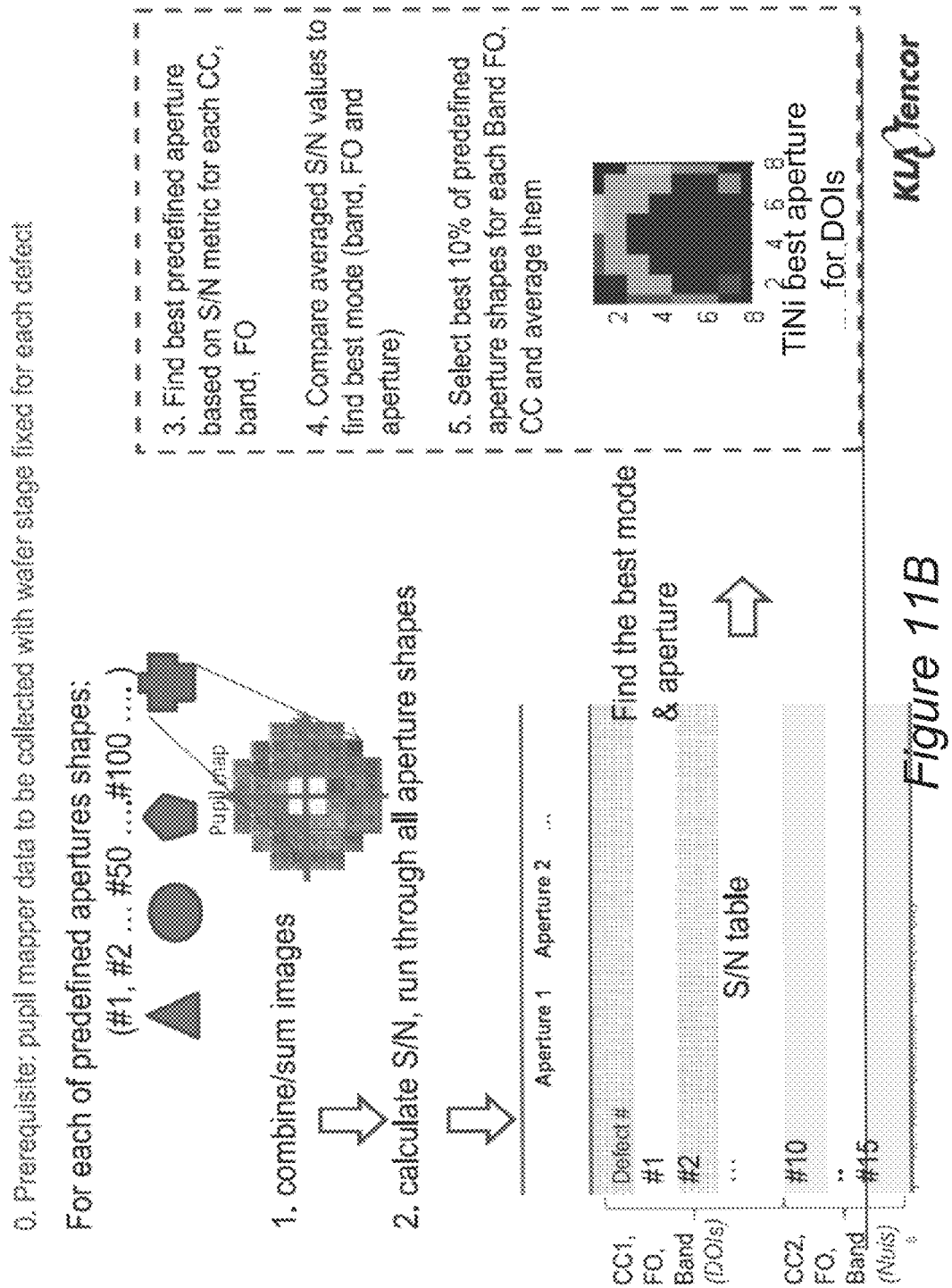
Figure 11C:
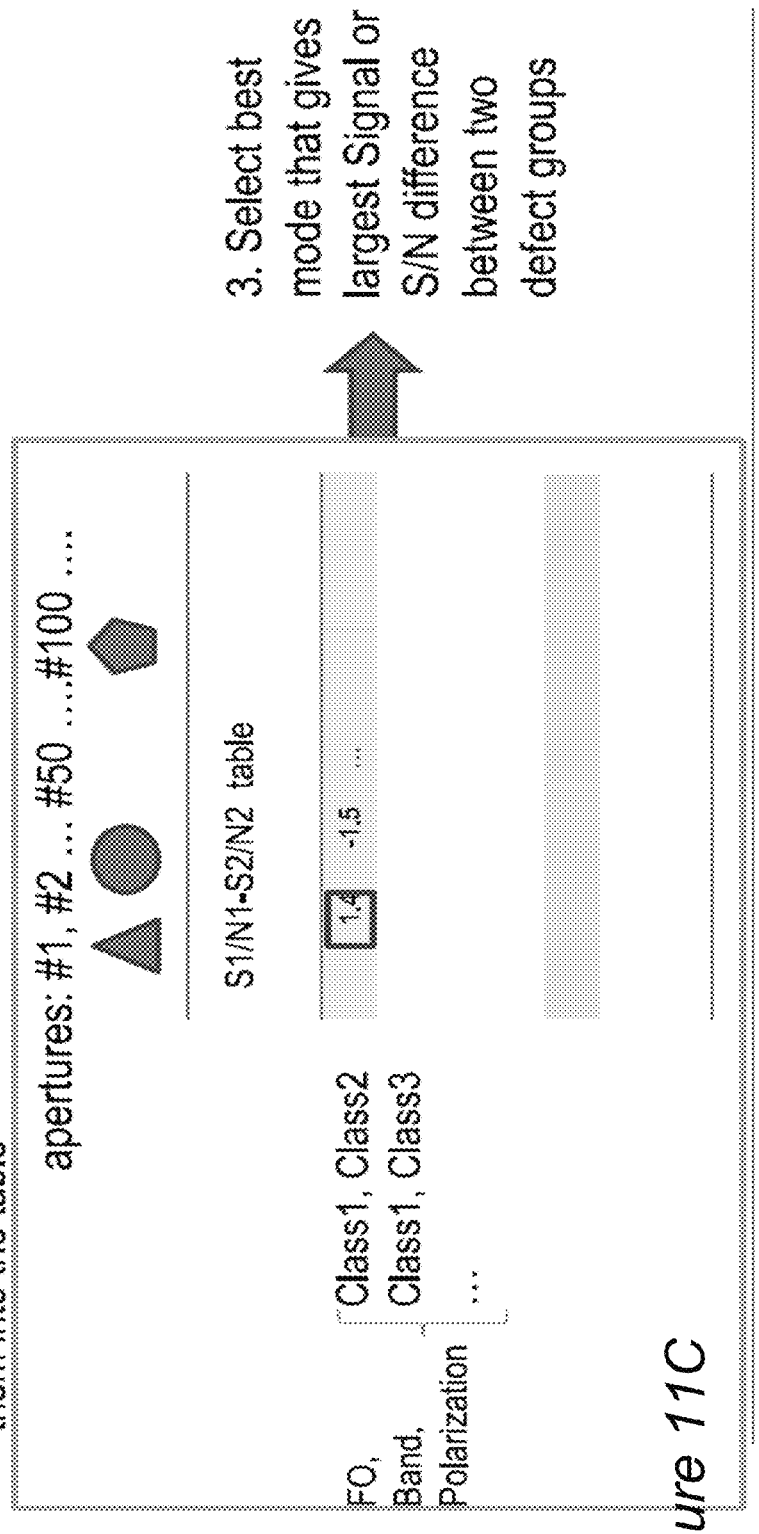

In further implementations, the above techniques can also be expanded to find a best mode of inspection tool operation. The best mode may pertain to any suitable operating parameter, such as aperture configuration, focus offset, wavelength band or spectrum, input polarization state, output polarization state, etc. FIGS. 11A-11C illustrate processes for determining a best mode in accordance with one embodiment of the present invention. In one embodiment, the aperture configurations are selected from a predefined set of aperture templates. FIG. 11A illustrates finding the best mode that gives the highest S/N ratio (or signal) for an individual defect or individual group/class of defects. A set of best aperture configurations (e.g., top 10%) may also be determined for each mode (focus offset, band, polarization states) and across classes of defects as shown in FIG. 11B. FIG. 11C illustrates selecting one or more optimum apertures across different classes of defects. In this example, the mode that gives the best S/N difference between defect groups/classes is selected.

Figure 12B:
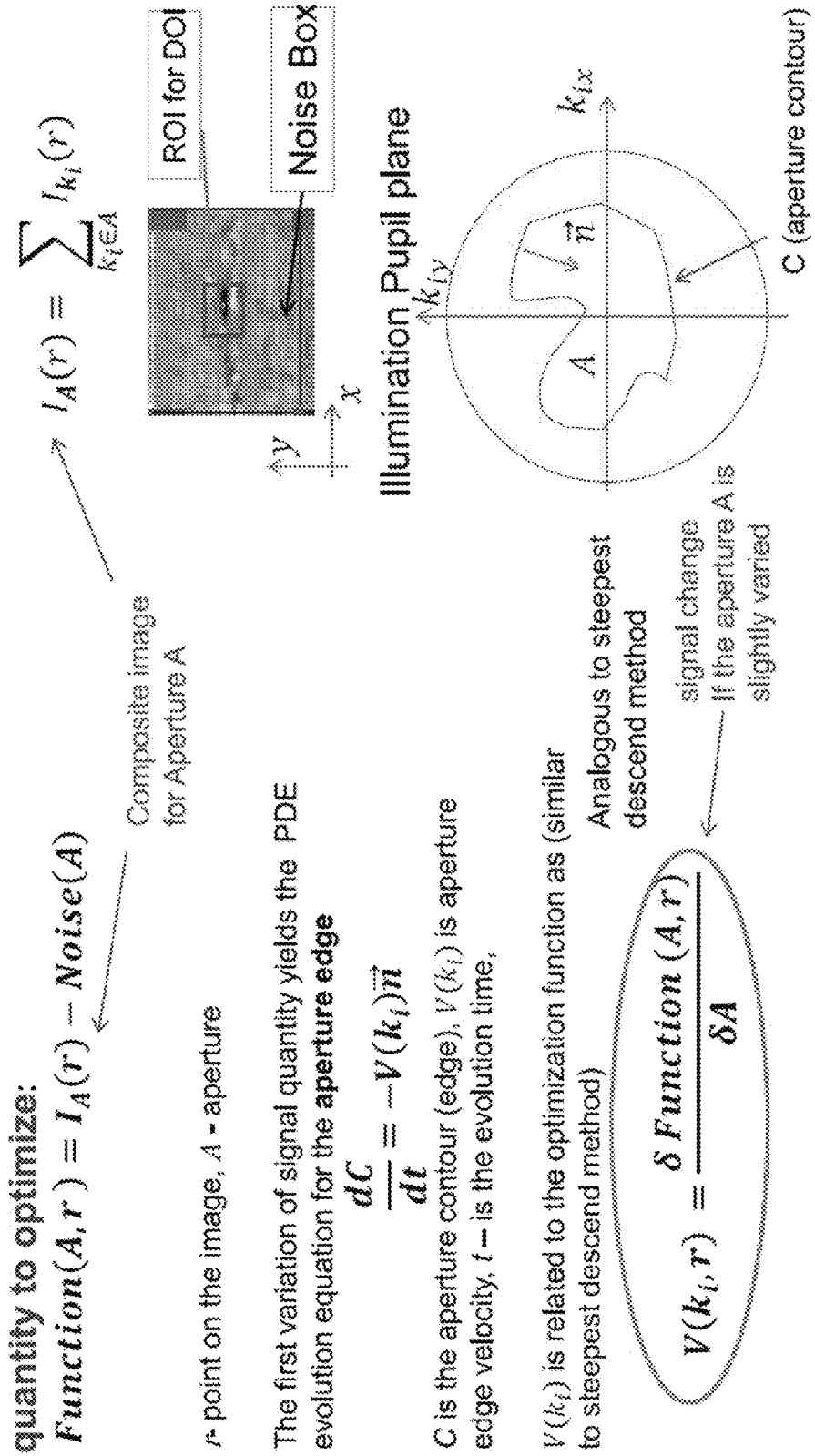

In another technique, a best mode is found by simulating an aperture configuration and evolving the simulated aperture edges as shown in FIG. 12A-B. An aperture segmentation algorithm may be used to evolve simulated aperture edges. In this optimization technique, an aperture configuration's shape and edge evolution are represented with an equation, such as a partial differential equation (PDE). The aperture equation also describes the aperture's edge going through an evolving process so as to maximize (or minimize) an optimization quantity for an image or signal generated with such evolving aperture configuration. In general, the evolution equation defines each point on the aperture configuration's edge (e.g., each point on the perimeter of the aperture's shape). The equation is adjusted so that the aperture edge moves or one or more points on the edge incrementally move. The equation can be adjusted to move one or more points on the aperture edge to the interior of the aperture so the aperture shape becomes smaller or to move the aperture edge out so the aperture shape becomes larger.

A defect detection characteristic, such as S/N ratio, may then be determined and analyzed for an image or signal that is simulated for each adjusted aperture shape. The aperture shape that results in the best defect detection shape may then be defined as the optimum aperture configuration. Additionally, the defect detection characteristic and corresponding aperture combination may be optimized for different modes and one or more defect classes.

For each aperture shape or edge evolution increment, an image may be simulated for a particular defect area. The simulated defect position in the simulated image may optically shift based on different illumination angles from different aperture configurations, for example. Accordingly, each point in a region of interest (ROI) may be analyzed for signal strength/intensity, as compared to a noise signal strength value (e.g., average of signal outside ROI). The noise signal strength should be defined as the standard deviation of signal outside an ROI. For example, a ROI may have 400 points to analyze for each aperture shape. The point and aperture shape that results in the best S/N ration or S-N difference may be defined as the defect and best aperture configuration.

An aperture evolution approach allows an optimum aperture configuration to be found that is not necessarily a part of the inspection tool's set of predefined apertures. However, this approach may be slower than the other approaches that work with predefined apertures because the equation can iterate through a larger number of aperture shapes before finding an optimum aperture configuration.

A PDE equation may be used to represent an initial circle aperture that partially covers a portion of the pupil (or Fourier area). The equation is then adjusted so that one or more points on the perimeter of this initial circle are then evolved to find the best aperture configuration. Since a global optimization for the entire pupil area, for example, is being located with this evolution approach, it does not matter which initial aperture is chosen.

In another combined technique, an optimum aperture from a predefined aperture list may first be analyzed by summing simulated or measured images for individual aperture positions to find the best predefined aperture configuration. The best predefined aperture may then be evolved and a resulting simulated image or signal analyzed to find the final optimum aperture configuration, which may differ from the best predefined aperture.

Certain embodiments provide efficient techniques for determining an optimum primary mode for semiconductor wafer inspection without iterating through a high number of modes. For example, a primary mode may be found without obtaining images or signals from all of the modes from which the primary mode is selected. Instead, images or signals may be generated for a subset of modes and used to assess the subset of modes, as well as other modes for which signals or images are not generated.

The primary mode is generally selected to provide a high ratio of defect signals to noise signals or some other optimum inspection characteristic. However, some of the defect signals may correspond to defect-of-interest (DOI) signals, while other defect signals may pertain to nuisance signals. That is, a portion of the DOI signals that are generated using the selected primary mode may be similar in strength to a portion of nuisance signals that are also generated using the same selected primary mode. In sum, the selected primary mode may not allow some of the DOIs to be distinguished from some of the nuisance defects.

In an alternative technique, two or more different modes (e.g., aperture, spectral band, input and output polarization, and focus offset) may be found so that the results from such multiple modes can be fused together so as to more effectively separate the DOI signals from the noise signals. In general, a combination of modes that facilitates separation between DOI's and noise (or other types of defects) during inspection is found.

By way of example, a secondary mode that results in different responses in the DOI and nuisance signals, as compared with the DOI and nuisance responses in the primary mode, may be found for combining with the selected primary mode. For example, a selected secondary mode that has weak DOI intensity signals and strong nuisance intensity signals may also be found for combining with a selected primary mode that otherwise would result in both strong DOI and nuisance intensity signals. In another example, a selected secondary mode that has strong DOI intensity signals and weak nuisance intensity signals may also be found for combining with a selected primary mode that otherwise would result in both strong DOI and nuisance intensity signals. The former example secondary mode having a strong DOI signal may be analyzed together with a primary mode having both strong DOI and nuisance signals to achieve a better overall DOI capture/detection, than analyzing only the results from this type of secondary mode.

Figure 13:
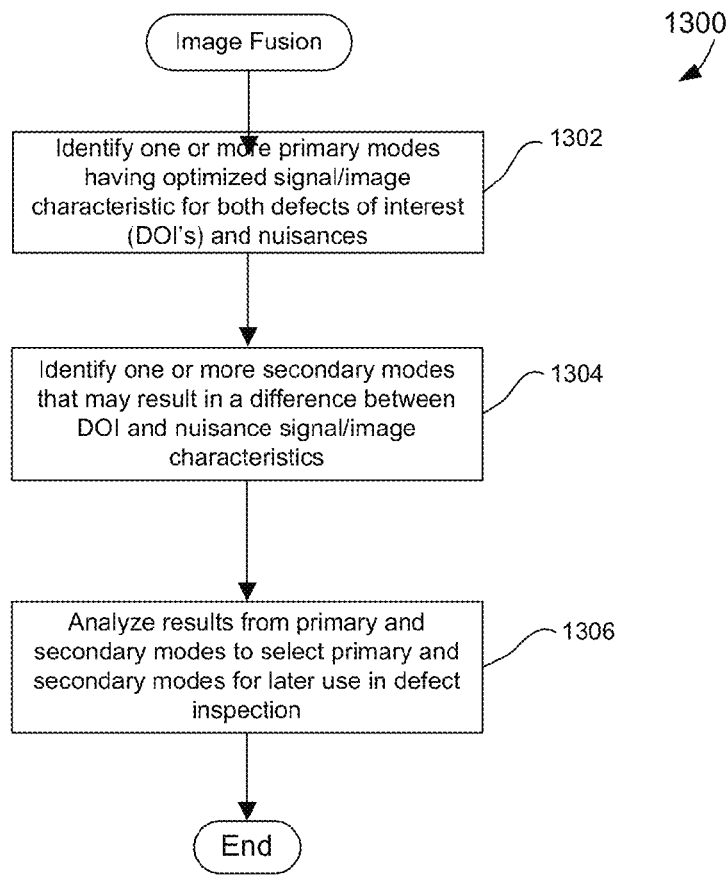
FIG. 13 is a flowchart illustrating a process for combining two or more modes in accordance with one or more embodiments of the present invention.

FIG. 13 is a flowchart illustrating a process 1300 for combining two or more modes in accordance with one or more embodiments of the present invention. Initially, one or more primary modes that each have an optimized signal or image characteristic for both defects of interest (DOI's) and nuisances may be identified in operation 1302. For instance, one or more primary modes may have been found using any of the mode determination techniques described herein, such as simulating the results of combining illumination and/or collection apertures.

Figure 14:
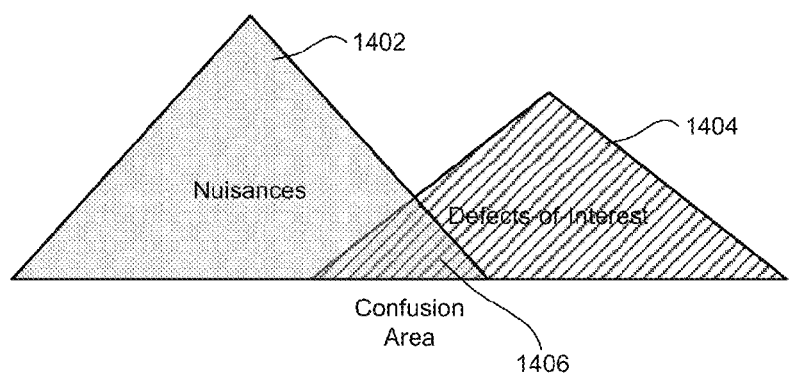
FIG. 14 illustrates DOI and nuisance populations that overlap.

An identified primary mode may have a maximized signal to noise ratio (SNR) for the defects-of-interest (DOI's), as well as a nuisance to noise ratio. FIG. 14 illustrates DOI and nuisance signals or populations that overlap in the defect results obtained with a particular primary mode. As shown, an overlapping DOI and nuisance area or "confusion area" 1406 is present between the nuisance population 1402 and the DOI population 1404. It may be difficult to distinguish between nuisances and DOI signals in this confusion area 1406 since the nuisance and DOI signals are similar to each other in this confusion area 1406.

In certain embodiments, a secondary mode can be used together with the selected primary mode to allow separation of the nuisances from DOI's. In other aspects, mode combinations could be used to separate out various other detected signals, such as certain particular types or classes of DOI's, nuisances, etc. In one example, a secondary mode may result in a strong or maximized SNR for all or a selected subset of DOI's and a weak or minimized SNR for nuisances (e.g., nuisances disappear). Alternatively, the selected secondary mode may result in a weak SNR for all or a selected subset of DOI's and a strong SNR for the nuisances. A secondary mode may be selected for use with a primary mode to maximize the DOIs that are detected and captured while simultaneously minimizing the nuisance events that are detected, or visa versa.

A secondary mode may provide a distinction between DOI's and nuisances, and such distinction may be represented by various signal or image characteristics in the results of such secondary mode. By way of examples, signal or image characteristics of DOI's and/or nuisances (of a primary and/or secondary mode) may include one or more of the following: intensity value, image texture value, polarity (e.g., whether the defect or background flips from negative to positive values), etc. Each signal or image characteristic may pertain to an area of a test sample containing a DOI or nuisance object or a corresponding reference area that does not contain a DOI or nuisance object, or a difference signal/image of the test and reference area signals/images.

In the illustrated embodiment, one or more secondary modes that may result in a difference between the DOI and nuisance signal or image characteristics may be identified in operation 1304. In one embodiment, a subset of the modes used to determine the one or more primary modes is identified as secondary modes. Alternatively or additionally, the identified secondary modes may include other modes that differ from the primary mode. At least one or more secondary modes will differ from the one or more primary modes since the primary modes fail to distinguish between DOI's and nuisances, and the goal is to find at least one secondary mode that distinguishes between DOI's and nuisances.

Regardless of the techniques for identifying the one or more primary modes and obtaining results for one or more secondary modes, the results from the primary and secondary modes may then be analyzed to select primary and secondary modes for later use in defect inspection in operation 1306. This analysis may include finding one or more secondary modes that result in the greatest distinction between the DOI's and nuisances or analyzing the combined results from various subsets of primary and secondary modes to determine which combination results in maximum capture of DOI's and minimum capture of nuisances.

Figure 15:
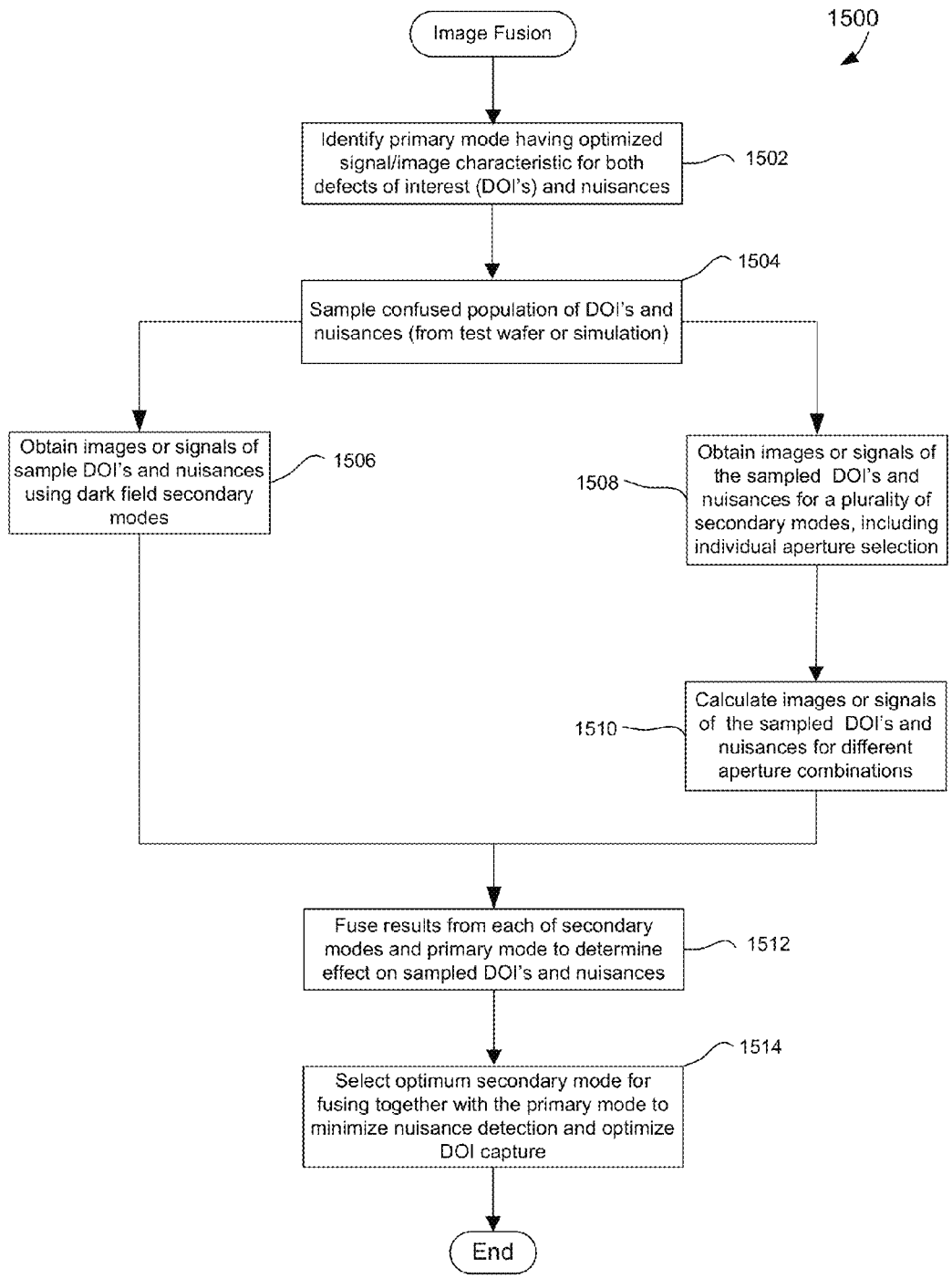
FIG. 15 is a flow chart illustrating a detailed procedure for determining two or more modes from which results can be fused for optimal defect detection in accordance with one embodiment of the present invention.

FIG. 15 is a flow chart illustrating a detailed procedure 1500 for determining two or more modes from which results can be fused for optimal defect detection in accordance with a specific embodiment of the present invention. As shown, a primary mode having optimized signal/image characteristics for both DOI's and nuisances is identified in operations 1502. Identification of the primary mode is based on which mode is deemed optimum for a particular set of known DOI's, which are obtained from a test wafer or are simulated. The identified primary mode results in at least some of this particular set of known DOI's being also confused with at least a portion of a population of nuisance events. This "confused" population of DOI's and nuisances can be sampled in operation 1504 to efficiently find one or more secondary modes that will result in separating this confused population.

Signals or images may be obtained for any suitable number and type of secondary modes. For instance, the secondary modes (and primary modes) may include one or more darkfield modes, as well as brightfield modes. Additional modes may be utilized as described further herein.

As shown, images or signals of the sample DOI's and nuisances may be obtained using darkfield secondary modes in operation 1506. The darkfield modes may include different illumination apertures and collection apertures for collecting scattered light from the sample, as well as different polarizations, spectrum, focus, etc. In each darkfield mode, light is illuminated in a particular portion of the pupil (e.g., edge portion), which results in the illumination beam hitting the sample at corresponding incident angles. Scattered light is collected at a different portion (e.g., center) and collection angles, as compared to the selected illumination pupil portion and incident angles.

Different combinations of illumination and collection angles may be used in the different secondary (and/or primary) modes. However, the resulting images or signals for darkfield modes are not additive so as to predict results for other modes in the same way that may be achieved with respect to results obtained from brightfield individual aperture modes, for example. That is, the image or signals from individual darkfield modes would typically not be combined together to predict the resulting signals or images that were not actually collected by the inspection tool's detectors or cameras.

The secondary (and/or primary) modes may also include brightfield modes having different individual illumination apertures, as well as simulated modes for which the resulting images or signals are predicted based on combining different ones of the individual illumination aperture results as further described herein. As shown, images or signals of the sampled DOI's and nuisances are also obtained for a plurality of secondary modes that include individual aperture selection, as well as other inspection parameters, in operation 1508. Images or signals of the sampled DOI's and nuisances (from a test sample or simulated) may then be calculated for different secondary modes that include different aperture combinations in operation 1510.

The results from each secondary and primary mode may then be fused (or analyzed together) to determine the effect on DOI's and nuisances in operation 1512. The optimum secondary mode, which is to be fused together with a primary mode, may then be selected to minimize nuisance detection and optimize (or maximize) DOI capture in operation 1514. The results from any number of primary and secondary modes may be fused together and any signal or image characteristic from the fused results may be analyzed to find the optimum secondary mode(s).

The secondary mode that results in a maximized separation of the DOI's from the nuisances may be selected after combining the results from all combinations of the primary mode and the secondary modes. That is, the secondary mode that results in a maximized number of detected known DOI's while excluding a maximized number of known nuisances from a sample can then be utilized in combination with the primary mode to detect unknown DOI's on an unknown sample.

Figure 16:
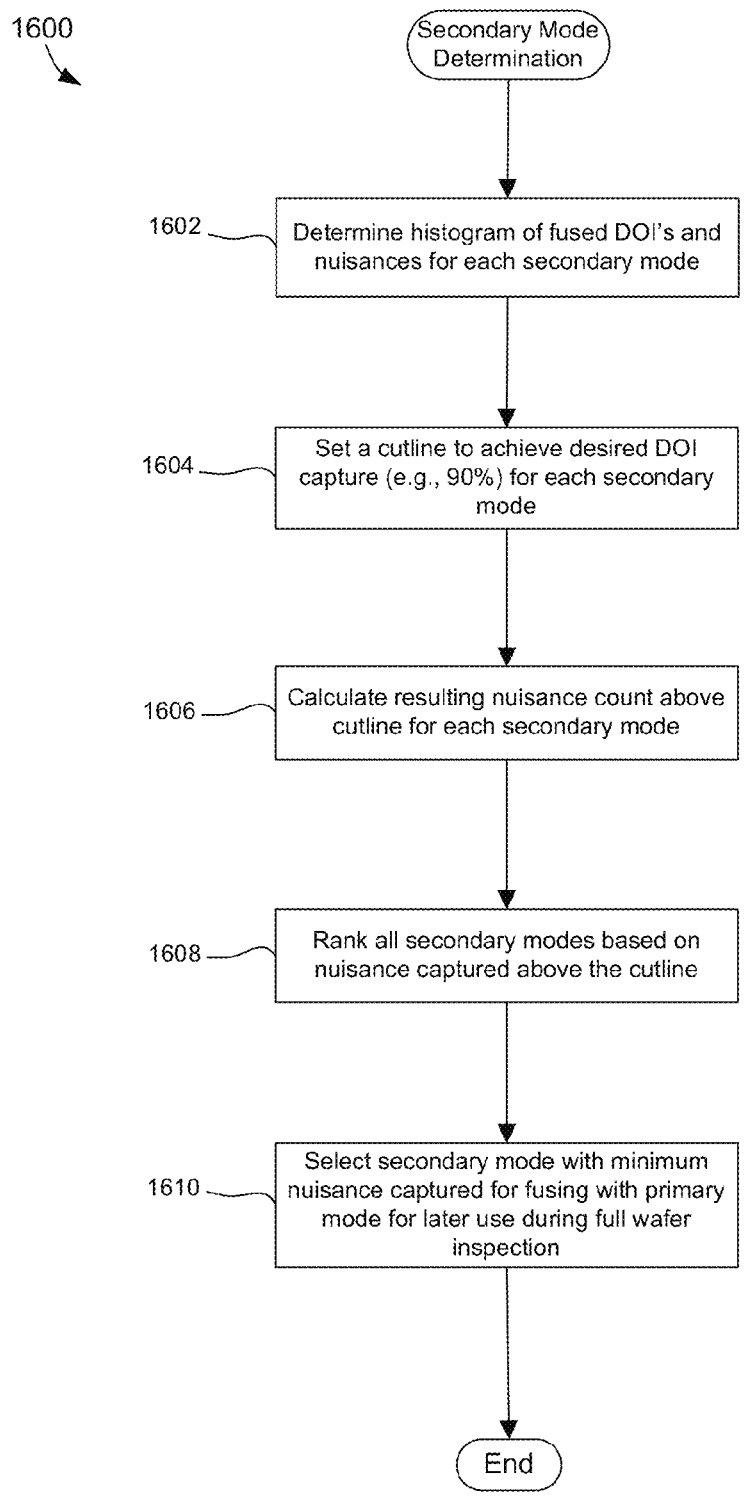
FIG. 16 is a flow chart illustrating a procedure 1600 for determining an optimum secondary mode in accordance with a specific implementation of the present invention.
Figure 17:
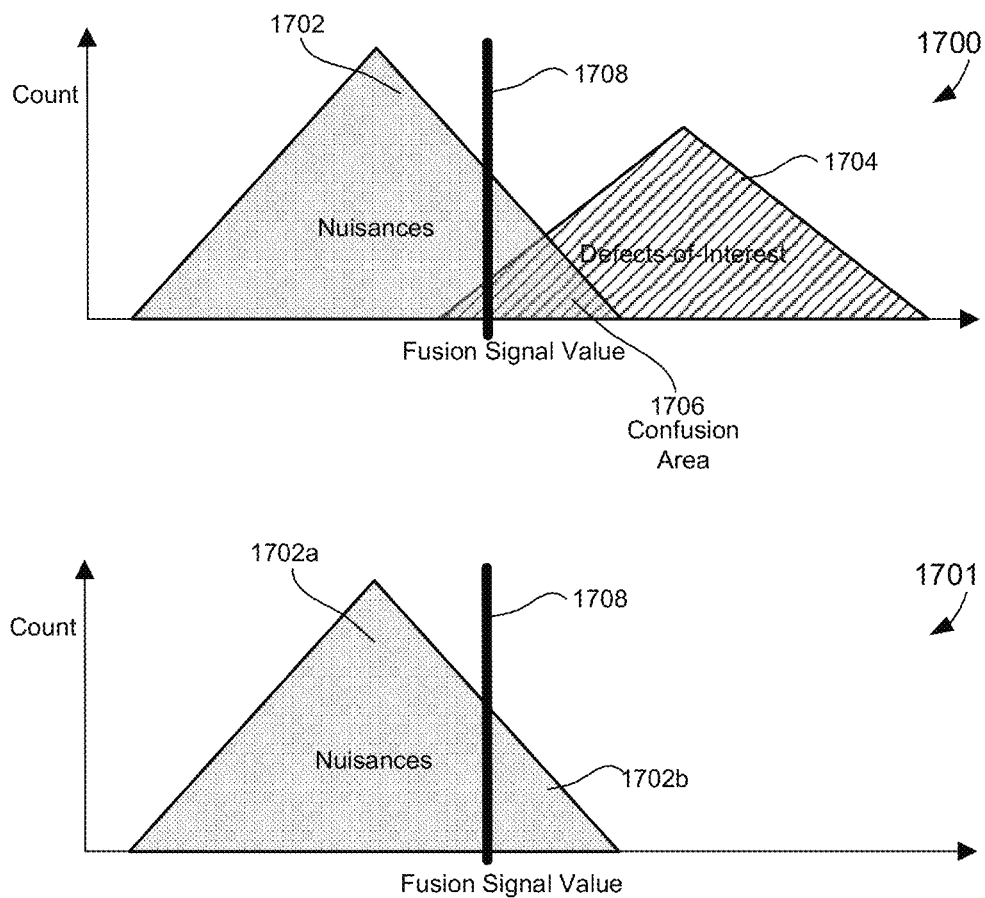
FIG. 17 is a diagrammatic representation of the technique of FIG. 16 for determining an optimum secondary mode for fusing with a primary mode in accordance with one embodiment of the present invention.

FIG. 16 is a flow chart illustrating a procedure 1600 for determining an optimum secondary mode in accordance with a specific implementation of the present invention. FIG. 17 is a diagrammatic representation of the technique of FIG. 16 for determining an optimum secondary mode for fusing with a primary mode in accordance with one embodiment of the present invention. A histogram 1700 (or any other suitable metric) of fused DOI's and nuisances for each secondary mode may initially be determined in operation 1602. The histogram of FIG. 17 includes counts for both DOI's and nuisances as a function of a fusion signal value. As shown in FIG. 17, the DOI's population 1704 overlaps with the nuisance population 1702 within "confusion area" 1706.

A cutline 1708 may be set to achieve a desired (or predefined) DOI capture rate (e.g., 90%) for each secondary mode in operation 1604. The resulting nuisance count above the cutline 1708 may then be calculated for each secondary mode in operation 1606. Graph 1701 of FIG. 17 illustrates the nuisances for a particular secondary mode with respect to the selected cutline 1708. For instance, a first portion of nuisances 1702b remain above the cutline 1708, while a second portion of nuisances 1702a remain the cutline 1708.

All secondary modes may then be ranked based on the nuisances that are captured above the cutline in operation 1608. In operation 1610, a secondary mode with minimum nuisance captured above the cutline may then be selected for fusing with the primary mode for later use during a full wafer inspection, for example. The procedure for determining a secondary mode may then end.

The results from the primary and secondary modes may be used to distinguish between DOI's and nuisance in any suitable manner. In the example in which the selected secondary mode has a strong SNR for the DOI's and a weak SNR for the nuisances, objects that have strong SNR in both modes may be defined as DOI's, while objects that do not have strong SNR in both modes would be excluded as mere nuisances. If a secondary mode is chosen that results in a strong SNR for nuisances and a weak SNR for DOI's, objects that have strong SNR in both modes may be excluded and defined as nuisances, while any remaining objects are defined as DOI's. In another technique for any secondary mode that has a signal distinction between DOI's and nuisance objects, objects that have a strong correlation in the primary and secondary modes can be defined as DOI's.

The techniques for selecting one or more primary and secondary modes described herein may be implemented at any suitable time for selecting an inspection mode. The selected one or more modes can then be utilized to inspect any number and type of samples. In some embodiments, one or more inspection modes are found for each particular inspection tool, and the selected mode(s) are used to inspect all semiconductor samples with the particular inspection tool. Modes may also be selected for each fabrication process or each semiconductor design and/or process.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A method for optimizing a mode of an inspection tool, comprising:
   obtaining a first image or signal for each of a plurality of first apertures of the inspection tool, wherein each first image or signal pertains to a defect area;
   for each of a plurality of combinations of the first apertures and their first images or signals, obtaining a composite image or signal by combining the first images or signals obtained for each individual aperture in such combination;
   analyzing each composite image or signal to determine an optimum one of the combinations of the first apertures based on a defect detection characteristic of each composite image, wherein determining an optimum one of the combinations of the first apertures includes selecting a set of one or more individual apertures that result in the highest contrast for the defect area; and
   setting the optimum combination of the first apertures on the inspection tool and inspecting a sample using such optimum combination of the first apertures.

2. The method of claim 1, wherein each first image or signal is obtained from experimental data from a sample using each of the first apertures in the inspection.

3. The method of claim 1, wherein each first image or signal is obtained from a simulation model for the inspection tool obtaining the first image or signal using each first aperture.

4. The method of claim 1, wherein the first apertures are positioned at a plurality of positions across a pupil or Fourier plane of the inspection tool.

5. The method of claim 4, wherein the first apertures are positioned to provide full angular coverage for an incident beam generated by the inspection tool that impinges on the defect area, wherein the first apertures have a number that is greater than 100.

6. The method of claim 1, wherein the first apertures together cover a substantial portion of the pupil or Fourier plane of the inspection tool.

7. The method of claim 1, wherein composite images are obtained for all combinations of the first apertures by summing the first images for each combination.

8. The method of claim 1, wherein the defect detection characteristic is a defect of interest (DOI) signal to noise signal ratio or a difference between a DOI signal and a noise signal, and the optimum combination of the first apertures has a composite image having a maximum DOI signal to noise signal or a maximum difference between a DOI signal and a noise signal.

9. The method of claim 8, wherein the defect detection characteristic is determined for each of plurality of points within a region of interest (ROI) of each composite image.

10. The method of claim 1, wherein the first images are further obtained for a plurality of modes having different combinations of wavelength range settings, focus offset settings, and input and output polarization states, and wherein the composite images are further obtained for each of the modes.

11. The method of claim 10, wherein the first images are obtained for a plurality of defect classes, and wherein the composite images are further obtained for each of the defect classes.

12. The method of claim 10, wherein a plurality of optimum combinations of the first apertures are determined for two or more optimum ones of the modes that will together result in a separation of defect classes.

13. The method of claim 12, wherein the separation of defect classes comprises a separation between DOI's and nuisance defects.

14. A method of facilitating an inspection of a sample using an optical inspection tool, the method comprising:
   simulating opening an aperture of a plurality of apertures in the inspection tool one at a time at each of a plurality of aperture positions that are spread across an illumination pupil area or a Fourier plane area;
   simulating an image or signal of one or more defect areas for each aperture position of the inspection tool;
   based on the simulated images and signals for each aperture position, determining a defect detection characteristic for each aperture position and determining a defect detection characteristic for each combination of aperture positions by combining the defect detection characteristics for each combination of aperture positions;
   determining an optimum aperture configuration based on the determined defect detection characteristic for each aperture position and the combined defect detection characteristics, wherein determining an optimum aperture combination includes selecting a set of one or more individual apertures that result in the highest contrast for the one or more defect areas; and
   setting the optimum aperture configuration on the inspection tool and inspecting a sample using such optimum aperture configuration.

15. The method of claim 14, wherein opening an aperture at each of the plurality of aperture positions is associated with different incident angles of a simulated incident beam directed towards the one or more defect areas.

16. The method of claim 14, wherein opening a plurality of apertures at the plurality of aperture positions is associated with different portions of a simulated output beam emanating from the one or more defect areas.

17. The method any of claim 14, wherein determining the defect detection characteristic for each aperture position and combination of apertures positions comprises:
   summing the images for each combination of aperture positions to obtain a plurality of composite images;
   for each aperture position, determining a signal to noise value based on such aperture's image;
   for each aperture combination determining a defect of interest (DOI) signal to noise signal ratio or a difference between a DOI signal and noise signal based on such aperture combination's composite image; and
   defining a particular one of the aperture combinations that has that has a maximum defect of interest (DOI) signal to noise signal ratio or a maximum difference between a DOI signal and noise signal as the optimum aperture configuration.

18. The method of any of claim 14, wherein the optimum aperture configuration is not yet available on the inspection tool, the method further comprising adding the optimum aperture configuration to the inspection tool.

19. An inspection system for inspecting a photolithographic reticle or wafer for defects, comprising:
a light source for generating an incident beam;
a configurable illumination pupil aperture module having a plurality of configurable apertures for receiving the incident beam;
an illumination optics module for directing the incident beam through the illumination aperture and onto a sample;
a collection optics module for directing an output beam that is emitted from the sample in response to the incident beam;
a sensor for detecting the output beam and generating an image or signal for the output beam; and
a controller that is configured to perform the following operations:
obtaining a first image or signal for each of a plurality of first apertures of the inspection tool, wherein each first image or signal pertains to a defect area;
for each of a plurality of combinations of the first apertures and their first images or signals, obtaining a composite image or signal by combining the first images or signals obtained for each individual aperture in such combination;
analyzing each composite image or signal to determine an optimum one of the combinations of the first apertures based on a defect detection characteristic of each composite image, wherein determining an optimum one of the combinations of the first apertures includes selecting a set of one or more individual apertures that result in the highest contrast for the defect area; and
setting the optimum combination of the first apertures on the inspection tool and inspecting a sample using such optimum combination of the first apertures.

20. The system of claim 19, wherein each first image or signal is obtained from experimental data from a sample using each of the first apertures in the inspection.

21. The system of claim 19, wherein each first image or signal is obtained from a simulation model for the inspection tool obtaining the first image or signal using each first aperture.

22. The system of claim 19, wherein the first apertures are positioned at a plurality of positions across a pupil or Fourier plane of the inspection tool and wherein the first apertures are positioned to provide full angular coverage for an incident beam generated by the inspection tool that impinges on the defect area, wherein the first apertures have a number that is greater than 100.

23. The system of claim 19, wherein composite images are obtained for all combinations of the first apertures by summing the first images for each combination.

* * * * *